(12) United States Patent
Cooper et al.

(10) Patent No.: US 8,148,404 B2
(45) Date of Patent: Apr. 3, 2012

(54) MODULATORS OF CB1 RECEPTORS

(75) Inventors: Martin Cooper, Hoersholm (DK); Jean-Marie Receveur, Hoersholm (DK); Thomas Hoegberg, Hoersholm (DK); Peter Aadal Nielsen, Hoersholm (DK); Jean-Michel Linget, Hoersholm (DK); Pia Karina Noeregaard, Hoersholm (DK); Anthony Murray, Hoersholm (DK); Emelie Bjurling, Hoersholm (SE)

(73) Assignee: 7TM Pharma A/S (DK)

( * ) Notice: Subject to any disclaimer, the term of this patent is extended or adjusted under 35 U.S.C. 154(b) by 66 days.

(21) Appl. No.: 12/518,446

(22) PCT Filed: Dec. 17, 2007

(86) PCT No.: PCT/GB2007/004842
§ 371 (c)(1),
(2), (4) Date: Nov. 2, 2009

(87) PCT Pub. No.: WO2008/075019
PCT Pub. Date: Jun. 26, 2008

(65) Prior Publication Data
US 2010/0144701 A1    Jun. 10, 2010

(30) Foreign Application Priority Data

Dec. 18, 2006 (GB) .................................. 0625197.9
Sep. 14, 2007 (GB) .................................. 0717998.9

(51) Int. Cl.
*A61K 31/445* (2006.01)
*C07D 401/14* (2006.01)
(52) U.S. Cl. ........ 514/326; 546/184; 546/192; 546/211; 514/315; 514/317
(58) Field of Classification Search .................. 546/184, 546/192, 207, 211; 514/315, 317, 326
See application file for complete search history.

(56) References Cited

U.S. PATENT DOCUMENTS 5,624,941 A * 4/1997 Barth et al. .................. 514/326
5,744,491 A * 4/1998 Boigegrain et al. ........... 514/341
7,183,306 B2 * 2/2007 Shirai et al. .................. 514/406

FOREIGN PATENT DOCUMENTS

| EP | 0477049 A1 | 3/1992 |
| WO | 2004099157 A1 | 11/2004 |
| WO | 2005000820 A2 | 1/2005 |

* cited by examiner

OTHER PUBLICATIONS

International Search Report dated cited in PCT/GB2007/004842 on Mar. 19, 2008.

*Primary Examiner* — Golam M M Shameem
(74) *Attorney, Agent, or Firm* — Banner & Witcoff, Ltd.

(57) ABSTRACT

Compounds of formula (I) suppress the normal signalling activity CB1 receptors, and are thus useful in the treatment of diseases or conditions which are mediated by CB1 receptor signalling activity, such as treatment of obesity and overweight, prevention of weigh gain, treatment of diseases and conditions directly or indirectly associated with obesity and overweight: wherein $A_1$ is hydrogen, —COOH, or tetrazolyl; p and q are independently 0 or 1; A3 is phenyl or cycloalkyl, either of which is optionally substituted with $R_4$ and/or $R_5$; $R_4$ and $R_5$ are independently —$R_9$, —CN, —F, —Cl, —Br, —$OR_9$, —$NR_7R_8$, —$NR_7COR_6$, —$NR_7SO_2R_6$, —$COR_6$, —$SR_9$, —$SOR_9$, or —$SO_2R_6$; $R_6$ is $C_1$-$C_4$ alkyl, cycloalkyl, —$CF_3$ or —$NR_7R_8$; $R_7$ and $R_8$ are independently hydrogen, $C_1$-$C_4$ alkyl or cycloalkyl; $R_9$ is hydrogen, $C_1$-$C_4$ alkyl, $C_1$-$C_4$ alkoxy, $C_1$-$C_4$ alkoxy($C_1$-$C_4$ alkyl)-, cycloalkyl, or fully or partially fluorinated $C_1$-$C_4$ alkyl; $R_1$ (i) a bond; (ii) a divalent radical of formula —$(CH_2)_aB_1(CH_2)_b$ wherein a and b are independently O, 1, 2 or 3 provided that a+b is 1, 2 or 3, and $B_1$ is —CO—, -O-, —S—, —SO—, —SO$_2$—, —CH$_2$—, —CHCH$_3$—, —CHOH— or —NR$_7$—; or (iii) a divalent radical selected from —C(R$_{10}$)(R$_{11}$)—*, —C(R$_{10}$)(R$_{11}$)—O—*, —C(R$_{10}$)(R$_{11}$)CH$_2$—*, —C(R$_{10}$)(R$_{11}$)CH$_2$—O—*, —CH$_2$C(R$_{10}$)(R$_{11}$)—*, —CH$_2$C(R$_{10}$)(R$_{11}$)—O—*, —CH$_2$—O—C(R$_{10}$)(R$_{11}$)—* and —C(R$_{10}$)(R$_{11}$)—O—CH$_2$—*, wherein the bond indicated by an asterisk is attached to the pyrazole ring; Z is as defined in the specification; R$_{10}$ is hydrogen and R$_{11}$ is (C$_1$-C$_3$)alkyl or —OH; or R$_{10}$ and R$_{11}$ are both (C$_1$-C$_3$)alkyl; or R$_{10}$ and R$_{11}$ taken together with the carbon atom to which they are attached form a (C$_3$-C$_5$)cycloalkyl ring.

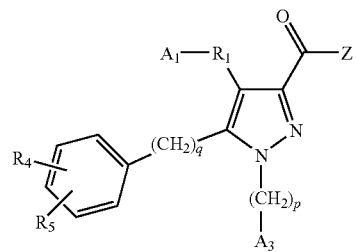

(I)

18 Claims, 1 Drawing Sheet

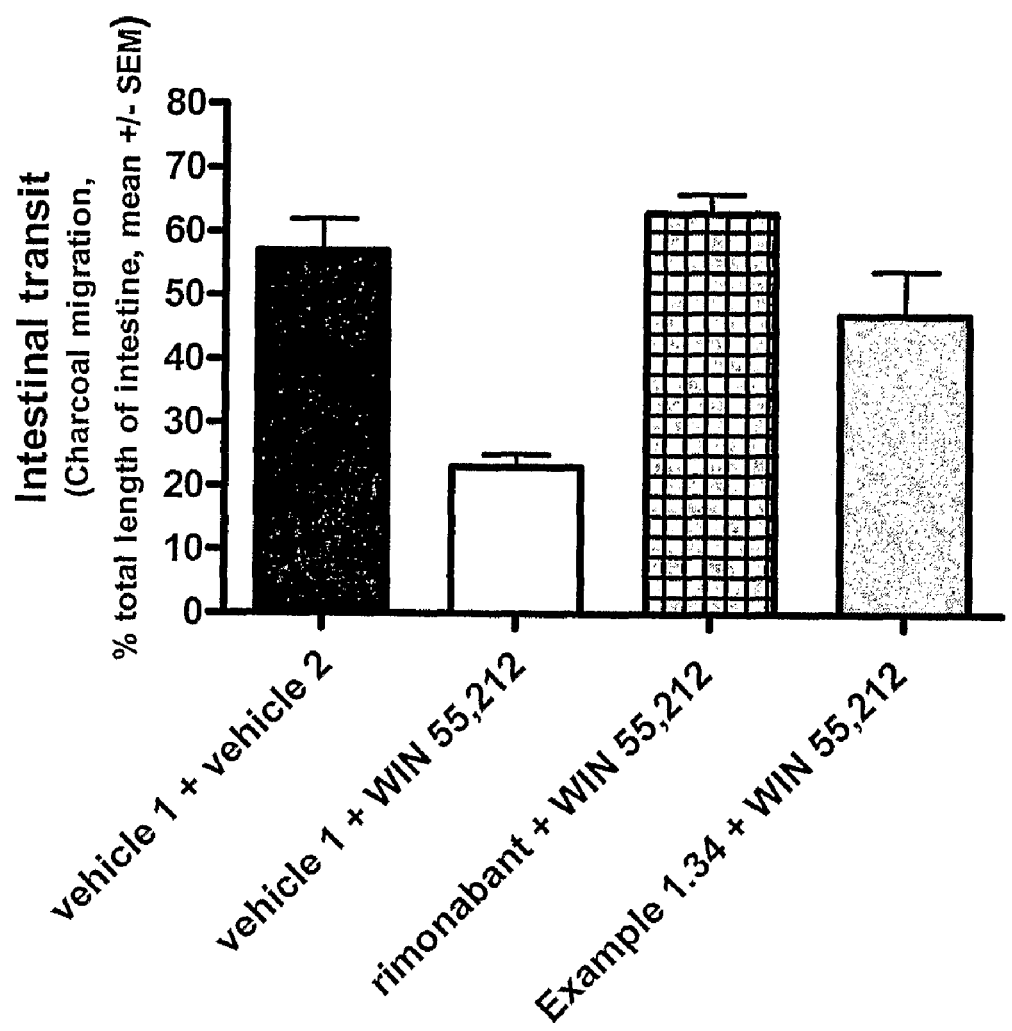

MODULATORS OF CB1 RECEPTORS

CROSS REFERENCE TO RELATED APPLICATIONS

This application is a National Stage application of co-pending PCT application PCT/GB2007/004842 filed Dec. 17, 2007, which claims the benefit of Great Britain application number 0625197.9 filed Dec. 18, 2006 and Great Britain application number 0717998.9 filed Sep. 14, 2007. These applications are incorporated herein by reference in their entireties.

The present invention relates to compounds which are modulators of cannabinoid receptor CB1 and which suppress the normal signalling activity of such receptors. The invention further relates to compositions and methods using said compounds for the treatment of diseases or conditions which are mediated by CB1 receptor signalling activity, such as treatment of obesity and overweight, prevention of weigh gain, treatment of diseases and conditions directly or indirectly associated with obesity and overweight such as metabolic syndrome, type 2 diabetes, cardiovascular disease, metabolic dysfunctions in obese, overweight or normoweight individuals, metabolic diseases or disorders, cancers, liver diseases and other secondary diseases referred to below, as well as for the treatment of some disorders not necessarily related to obesity and overweight, such as eating disorders, addictive disorders, mental disorders, neurological disorders, sexual dysfunctions, reproductive dysfunctions, liver diseases, fibrosis-related diseases and other clinical indications referred to below. The invention also relates to pharmaceutical compositions containing the compounds of the invention, and to the use of the compounds in combination with other treatments for such disorders.

BACKGROUND OF THE INVENTION

The prevalence of obesity in North America and in most European countries has more than doubled in the last 20 years and over half of the adult population are now either overweight or obese. Obesity is now recognized as a chronic disease and a critical global health issue (Fiegal et al, 1998, Int. J. Obesity 22:39-47, Mokdad et al, 1999, JAMA 282: 1519-1522; Halford, 2006, Appetite, 46, 6-10). The "identifiable signs and symptoms" of obesity include an excess accumulation of fat or adipose tissue, an increase in the size or number of fat cells (adipocyte differentiation), insulin resistance, increased glucose levels (hyperglycemia), increased blood pressure, elevated cholesterol and triglyceride levels and decreased levels of high-density lipoprotein. Obesity is associated with a significantly elevated risk for type 2 diabetes, coronary heart disease, stroke, hypertension, various types of cancer and numerous other major illnesses, and overall mortality from all causes (Must et al, 1999, JAMA 282:1523-1529, Calle et al, 1999, N. Engl. J. Med. 341:1097-1105). A cluster of metabolic risk factors for cardiovascular disease and type 2 diabetes is often referred to as metabolic syndrome, syndrome X or insulin resistance syndrome. The major components of metabolic syndrome X include excess abdominal fat (also known as visceral, male-pattern or apple-shaped adiposity), atherogenic dyslipidemia (decreased high-density lipoprotein cholesterol (HDL-C)), elevated triglycerides), hypertension, hyperglycaemia (diabetes mellitus type 2 or impaired fasting glucose, impaired glucose tolerance, or insulin resistance), a proinflammatory state and a prothrombotic state. (cf. AHA/NHLBI/ADA Conference Proceedings, Circulation 2004; 109:551-556). Other abnormalities often associated with the metabolic syndrome include increased apolipoprotein B concentrations, low adiponectin plasma levels, small dense low-density lipoprotein (LDL) particles, hyperuricaemia, non-alcoholic fatty liver disease/hepatic steatosis, elevated liver transaminases, gamma-glutamyl-transferase and microalbuminuria.

Like obesity, the prevalence of obesity-related diseases such as diabetes also continues to rise. Weight reduction is critical for the obese patient as it can improve cardiovascular and metabolic values to reduce obesity-related morbidity and mortality (Blackburn, 1999, Am. J. Clin. Nujtr. 69:347-349, Galuska et al, 1999, JAMA 282:1576). It has been shown that 5-10% loss of body weight can substantially improve metabolic parameters such as levels of fasting and post-prandial blood glucose, HbA1c (glycosylated haemoglobin), insulin, total plasma cholesterol, low density lipoproteins (LDL), triglyceride, uric acid and blood pressure and reduce the risk for development of diabetes, cancer and cardiovascular diseases (Goldstein, 1992, J. Obesity, 6, 397-415).

Thus, a primary aim of treatment for obesity, and obesity-related disorders, is weight loss. Initially, treatments are based on diet and lifestyle changes augmented by therapy with pharmacological therapies. However, while physical exercise and reductions in dietary intake of calories can improve the obese condition, compliance with this treatment is very poor because of sedentary lifestyles and excess food consumption, especially high fat containing food. Additionally, treatment with the available pharmacological therapies to facilitate weight loss fail to provide adequate benefit to many obese patients because of experienced side effects, contraindications, or lack of positive response. Hence, there is impetus for developing new and alternative treatments for management of obesity.

Several potential anti-obesity agents are currently investigated (for a review, see Bays, 2004, Obesity Research, 12, 1197-1211) such as i) central nervous system agents that affect neurotransmitters or neural ion channels (e.g. antidepressants (bupropion), noradrenaline reuptake inhibitors (GW320659), selective 5HT 2c receptor agonists, antiseizure agents (topiramate, zonisamide), some dopamine antagonists, cannabinoid CB-1 receptor antagonists (rimonabant);

ii) leptin/insulin/central nervous system pathway agents (e.g. leptin analogues, leptin transport and/or receptor promoters, CNTF (Axokine), NPY antagonists, AgRP antagonists, POMC promoters, CART promoters, MSH analogues, MC4 receptor agonists, agents that affect insulin metabolism/activity [PTP-1B inhibitors, PPAR receptor antagonists, short-acting D2 agonist (ergoset), somatostatin agonists (octreotide), and adiponectin/Acrp30 (Famoxin or Fatty Acid Metabolic OXidation INducer)]);

iii) gastrointestinal-neural pathway agents (e.g. agents that increase CCK and PYY activity, agents that increase GLP-1 activity (extendin 4, liraglutide, dipeptidyl peptidase IV inhibitor), agents that decrease ghrelin activity, amylin (pramlinitide), neuropeptide Y agonists);

iv) agents that may increase resting metabolic rate (beta-3 agonists, UCP homologues, thyroid receptor agonists); and v) other more diverse agents, such as for example including (MCH) melanin concentrating hormone antagonists, phytostanol analogues, functional oils, P57, amylase inhibitors, growth hormone fragments, synthetic analogues of DHEAS (fluasterone), antagonists of adipocyte 11beta-hydroxysteroid dehydrogenase type 1 activity, CRH agonists, carboxypeptidase inhibitors, inhibitors of fatty acid synthesis (cerulenin and C75), indanones/indanols, aminosterols (trodusquemine), and other gastrointestinal lipase inhibitors (ATL962).

Drugs effective in obesity treatment may act by various mechanisms such as by: a reduction of food intake (e.g. by inducing satiety or satiety signals), altering metabolism (e.g. by modifying the absorption of nutrients e.g. by inhibition of fat absorption), increasing energy expenditure (e.g. increase thermogenesis), inhibition of lipogenesis or stimulation of adipocyte apoptosis. However, only few drugs are available for obesity treatment (for reviews, see Gadde and Allison, 2006, Circulation, 114, 974-984; Weigle, 2003, J Clin Endocrinol Metab., 88, 2462-2469; Schioth, 2006, CNS Neurol. Disorders Drug Targets, 5, 241-249). Sibutramine is a centrally acting mixed inhibitor of serotonin and norepinephrine presynaptic re-uptake. Orlistat is an inhibitor of gastrointestinal lipases which reduces fat absorption in the gut. Rimonabant (SR141716, Acomplia®) is a centrally and peripherally acting cannabinoid CB1 modulator (antagonist and inverse agonist) that recently has been approved for treatment of obesity (for a review see Pagotto et al, 2006, Endocrine Reviews, 27, 73-100; for reports on phase III clinical trials see Despres et al, 2005, N. Engl. J. Med. 353, 212; van Gaal et al, 2005, Lancet, 16, 1389; Pi-Sunyer et al, 2006, JAMA, 295, 761).

Presently, two cannabinoid receptors have been characterized: CB1, a receptor found in the mammalian brain and in a number of other sites in peripheral tissues; and CB2, a peripheral receptor found principally in cells related to the immune system. For reviews on cannabinoid CB1 and CB2 receptor modulators, see Pertwee, 2000, Exp. Opin. Invest. Drugs, 9, 1553-1571 and Muccioli, 2005, Cur. Med. Chem., 12, 1361-1394. A substantial body of evidence indicates that CB1 antagonists (e.g. rimonabant) are able to modulate energy homeostasis and that CB1 antagonists are able to modulate food intake as well as peripherally block lipogenic processes (Pagotto et al, 2006, Endocrine Reviews, 27, 73-100; Tucci et al, 2006, Curr. Med. Chem. 13, 2669-2680; Lange and Kruse, 2004, Current Opinion in Drug Discovery & Dev., 7, 498-506). The peripheral effects of CB1 antagonists can be mediated by several target organs and mechanisms, e.g. i) liver: block of de novo lipogenesis, ii) muscles: increase in glucose uptake, iii) adipose tissue: stimulation of expression and/or secretion of adiponectin, inhibition of lipogenic enzymes, stimulation of GLUT4, generation of futile cycles, iv) pancreas: insulin regulation and v) gastrointestinal tract: stimulation of satiety signals.

Rimonabant (Acomplia®) is approved as an adjunct to diet and exercise for treatment of obesity. While the effects on body weight and metabolic parameters (plasma triglyceride levels, HDL cholesterol levels, plasma insulin levels, HbA1c [glycosylated haemoglobin] levels, insulin resistance, and adiponectin levels) are very encouraging, there are also undesirable side effects, possibly centrally mediated (psychiatric and nervous system disorders), such as anxiety, depressive disorders, sleep disorders, nausea, and vomiting (cf. http://emc.medicines.org.uk; http://www.emea.europa.eu/humandocs/PDFs/EPAR/acomplia/AcompliaEparScientificD-en-.pdf). Accordingly, there still exists a need for alternative CB1 receptor antagonists associated with differing pharmacokinetic, pharmacological, and side-effect profiles.

The CB1 receptor has been invoked in many disease states (cf. review by Pacher et al, 2006, Pharmacol. Rev, 58, 389-462). Modulators of CB1 receptor activity can be useful in the treatment of diseases and conditions associated with CB1 receptor regulation such as obesity and overweight, prevention of weight gain (e.g. induced by medications or smoking cessation), and in the treatment of diseases and conditions directly or indirectly associated with obesity (cf. Bray, 2004, J. Clin. Endocrinol. Metab. 89, 2583-9; Manson, et al, 1995, N. Engl. J. Med. 333, 677-85; Grundy, 2004, J. Clin. Endocrinol. Metab. 89, 2595-600; Esposito et al, 2004, JAMA 291; 2978-84; Ejerblad et al, 2006; J. Am. Soc. Nephrol. 17, 695-702; Whitmer et al, 2005, BMJ 330 (7504), 1360) such as metabolic syndrome, also referred to as syndrome X or insulin resistance syndrome, type 2 diabetes, cardiovascular diseases (e.g. aneurysms, angina, arrhythmia, atherosclerosis, cardiomyopathy, cerebrovascular accident (stroke), cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy and its associated arrhythmias and dizziness, mitral valve prolapse, myocardial infarction (heart attack), venous thromboembolism, varicose veins and pulmonary embolism, proinflammatory state, increased tendency to thrombosis (prothrombotic state), and intracranial hypertension, metabolic dysfunctions in obese, overweight or normoweight individuals (e.g. dyslipidemia, hyperlipidemia, low HDL and/or high LDL cholesterol levels, hypertriglycerideemia, low adiponectin levels, impaired glucose tolerance, insulin resistance, increase in HbA1c [glycosylated haemoglobin] levels, diabetes mellitus, type 2 diabetes, reduced metabolic activity), metabolic diseases or disorders (conditions in which there is a deviation from or caused by an abnormal metabolic process; can be congenital due to inherited enzyme abnormality or acquired due to disease of an endocrine organ or failure of a metabolically important organ such as the liver.), cancers (e.g. colorectal cancer, breast cancer, uterine cancer, colon cancer), liver diseases (e.g. non-alcoholic fatty liver disease, steatohepatitis, steatosis, hepatic fibrosis, hepatic cirrhosis), and other secondary diseases related to obesity and overweight, such as menstrual disorders, gastroesophageal reflux disease, cholelithiasis (gallstones), hernia, urinary incontinence, chronic renal failure, hypogonadism (male), stillbirth, stretch marks, acanthosis nigricans, lymphedema, cellulitis, carbuncles, intertrigo, hyperuricemia, immobility, osteoarthritis, low back pain, meralgia paresthetica, headache, carpal tunnel syndrome, dementia, idiopathic dyspnea, obstructive sleep apnea, hypoventilation syndrome, Pickwickian syndrome, asthma, depression, low self esteem, body dysmorphic disorder, social stigmatization.

The CB1 receptor has been invoked in many disease states diseases not necessarily related to obesity and overweight such as eating disorders, addictive disorders (e.g. addiction to marijuana, psychostimulants, nicotine, alcohol, cocaine, and opiates), mental disorders (e.g. schizophrenia, schizo-affective disorder, bipolar disorders, anxiety, panic disorder), neurological disorders, sexual dysfunctions (e.g. erectile dysfunction), reproductive dysfunctions (e.g. polycystic ovarian syndrome, infertility), liver diseases (e.g., viral hepatitis, liver dysfunction in other infectious diseases, inflammatory liver diseases (e.g. autoimmune hepatitis), alcoholic liver disease, toxic liver disease, liver tumors (such as liver cell carcinoma, hepatocellular carcinoma, hepatoma, cholangiocarcinoma, hepatoblastoma, angiosarcoma of liver, Kupffer cell sarcoma, other sarcomas of liver), steatohepatitis, non-alcoholic fatty liver disease hepatic fibrosis, hepatic cirrhosis, cirrhotic portal hypertension, metabolic liver diseases (such as haemochromatosis, Wilson's disease, Gilbert's syndrome, Crigler-Najjar syndrome, Dubin-Johnson syndrome, Rotor's syndrome)), fibrosis-related diseases (such as cystic fibrosis of the pancreas and lungs, endomyocardial fibrosis, idiopathic myocardiopathy, idiopathic pulmonary fibrosis of the lung, diffuse parenchymal lung disease, mediastinal fibrosis, myleofibrosis, post-vasectomy pain syndrome, retroperitoneal fibrosis, progressive massive fibrosis, proliferative fibrosis, neoplastic fibrosis, sickle-cell anemia may cause enlargement and ultimately fibrosis of the spleen), and other clinical indications such as epilepsy, osteoporosis, rheumatoid arthritis, inflammatory bowel disease (ulcerative colitis (UC) and Crohn disease (CD), congestive obstructive pulmonary disease (COPD), inflammation, inflammatory pain, atherosclerosis, diarrhoea, asthma, constipation, skin diseases, glaucoma and hair-loss.

Since obesity leads to, or significantly increases the risk of, co-morbidities involving various body systems (see Bays, 2004, Obesity Research, 12, 1197-1211) including:

i) cardiovascular (hypertension, congestive cardiomyopathy, varicosities, pulmonary embolism, coronary heart disease [CHD], neurological (stroke, idiopathic intracranial hypertension, meralgia parethetica), ii) respiratory (dyspnea, obstructive sleep apnea, hypoventilation syndrome, Pickwickian syndrome, asthma), iii) musculoskeletal (immobility, degenerative osteoarthritis, low back pain), iv) skin (striae distensae or "stretch marks," venous stasis of the lower extremities, lymphedema, cellulitis, intertrigo, carbuncles, acanthosis nigricans, skin tags), v) gastrointestinal (gastro-esophageal reflux disorder, non-alcoholic fatty liver/steatohepatitis, cholelithiasis, hernias, colon cancer), vi) genitourinary (stress incontinence, obesity-related glomerulopathy, breast and uterine cancer), vii) psychological (depression and low self-esteem, impaired quality of life), and viii) endocrine (metabolic syndrome, type 2 diabetes, dyslipidemia, hyperandrogenemia in women, polycystic ovarian syndrome, dysmenorrhea, infertility, pregnancy complications, male hypogonadism)

it is also useful to combine a CB1 modulator with medications used for treatment of such diseases. It is also useful to combine a CB1 modulator with medications used for treatment of diseases which may be unrelated to obesity such as eating disorders, addictive disorders, mental disorders, neurological disorders, sexual dysfunctions, reproductive dysfunctions, liver diseases, fibrosis-related diseases, and other clinical indications which may be unrelated to obesity.

BRIEF DESCRIPTION OF THE INVENTION

The present invention makes available a class of pyrazole compounds which modulate the activity of the cannabinoid receptor CB1. The following publications relate to other pyrazole compounds having CB1 modulatory activity:
WO1997021682, WO1997019063, WO2000046209, WO2001058869, WO200129007, WO2003088968, WO2003020217, WO2004052864, WO2005080343, WO2006067443, WO2006087480, WO 2006133926, EP00576357, EP00658546, US20030199536, US20040119972, US20040192667, US20050261281, US20050624941, US2006028084, US20060509367, J. Med. Chem. 1999 42, 769-776, Biochem. Pharmacol, 2000, 60, 1315-1323, J. Med. Chem. 2003, 46, 642-645, Bioorg & Med. Chem. Lett. 2004, 14, 2393-2395, Current Med. Chem. 2005, 12, 1361-1394.

As described herein, the compounds of the invention are useful for the treatment of obesity and overweight, prevention of weight gain, and in the treatment of diseases and conditions discussed above which benefit from suppression of the normal signalling activity of CB1 receptors. As mentioned, such diseases and conditions include obesity and overweight and those directly or indirectly associated with obesity and overweight (e.g. metabolic syndrome, type 2 diabetes, cardiovascular diseases, metabolic disorders, cancers, liver diseases, and other secondary diseases) as well as some which may be unrelated to obesity (e.g. eating disorders, addictive disorders, mental disorders, neurological disorders, sexual dysfunctions, reproductive dysfunctions, liver diseases, fibrosis-related diseases and other clinical indications). They are useful for modulating body weight and energy consumption in mammals and for modulating plasma parameters involved in the metabolic syndrome such as low HDL and/or high LDL cholesterol levels and/or small dense LDL particles, high triglyceride levels, low adiponectin levels and high HbA1c [glycosylated haemoglobin] levels and for modulating other characteristics of the metabolic syndrome such as impaired glucose tolerance, insulin resistance, excessive fat tissue in and around the abdomen, non-alcoholic fatty liver disease, steatohepatitis, steatosis, hepatic fibrosis, hepatic cirrhosis, liver tumors, metabolic liver diseases and high blood pressure.

The compounds of the invention display varying physicochemical properties and are useful for modulating peripheral CB1 receptors and to varying degree central CB1 receptors. Those compounds of the invention associated with a lowered central action on CB1 receptors may have a reduced propensity to induce psychiatric and nervous system side-effects.

Pending International Patent Application No PCT/EP2005/005726 relates to compounds having CB1 receptor modulatory activity of formula:

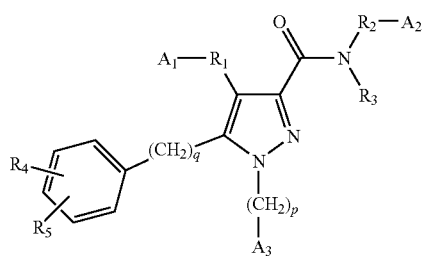

wherein
$A_1$ is hydrogen, —COOH, or tetrazolyl, and $A_2$ is hydrogen, —COOH, tetrazolyl, —CN, —CF$_3$, —COR$_6$, —SO$_2$R$_6$, —OR$_7$, —NR$_7$R$_8$, —NHCOR$_6$, or —NR$_7$SO$_2$R$_8$ provided that one of $A_1$ and $A_2$ is either
—COOH or tetrazolyl;

p is 0 or 1 and $A_3$ is phenyl or cycloalkyl, either of which is optionally substituted with $R_4$ and/or $R_5$;
q is 0 or 1;
$R_1$ is a bond, or —$(CH_2)_aB_1(CH_2)_b$— wherein a and b are independently 0, 1, 2 or 3 provided that a+b is not greater than 4, and $B_1$ is —CO—, —O—, —S—, —SO—, —$SO_2$—, —$CH_2$—, —CHOH— or —$NR_7$—.
$R_2$ is a bond, —$(CH_2)_aB_1(CH_2)_b$— or —$[(CH_2)_aB_1(CH_2)_b]_n$-$A_4$-$[(CH_2)_cB_2(CH_2)_d]_m$— wherein a, b, and $B_1$ are as defined for $R_1$; $B_2$ is as defined for $B_1$, c and d are independently 0, 1, 2 or 3; with the proviso that a+b+c+d is not greater than 6, n and m are independently 0 or 1 and $A_4$ is a monocarbocyclic or monoheterocyclic ring, having 3 to 8 ring atoms, optionally substituted with one or more of —F, —Cl, —Br, —CN, —$CF_3$, $C_1$-$C_4$ alkyl, cycloalkyl, —$OR_9$, oxo or —$NR_7R_8$;
$R_3$ is hydrogen, $C_1$-$C_4$ alkyl, cycloalkyl, —$OR_9$, —$NR_7R_8$, —$(CH_2)_sCOR_6$, —$(CH_2)_sSO_2R_6$, —$(CH_2)_sNR_7COR_6$, —$(CH_2)_sNR_7COOR_8$, —$(CH_2)_sNR_7SO_2R_6$, where s is 1, 2, 3 or 4;
$R_4$ and $R_5$ independently —$R_9$, —CN, —F, —Cl, —Br, —$OR_9$, —$NR_7R_8$, —$NR_7COR_6$, —$NR_7SO_2R_6$, —$COR_6$, —$SR_9$, —$SOR_9$, —$SO_2R_6$, —$(C_1$-$C_4$ alkyl)$OR_9$, —$(C_1$-$C_4$ alkyl)$NR_7R_8$, —$(C_1$-$C_4$ alkyl)$NR_7COR_6$, —$(C_1$-$C_4$ alkyl)$NR_7COOR_8$, —$(C_1$-$C_4$ alkyl)$NR_7SO_2R_6$, —$(C_1$-$C_4$ alkyl)$COR_6$, —$(C_1$-$C_4$ alkyl)$SO_2R_6$, —$NR_7COOR_8$, or —[N—$(C_1$-$C_4$ alkyl)]-tetrazolyl;
$R_6$ is $C_1$-$C_4$ alkyl, cycloalkyl, —$CF_3$ or —$NR_7R_8$;
$R_7$ and $R_8$ are independently hydrogen, $C_1$-$C_4$ alkyl or cycloalkyl; and
$R_9$ is hydrogen, $C_1$-$C_4$ alkyl, cycloalkyl, fully or partially fluorinated $C_1$-$C_4$ alkyl.

The compounds with which this invention is concerned differ in structure from those of PCTEP2005/005726 principally in the identity of the —$R_1$— radical and/or —$N(R_2)$—$R_3$-$A_2$ group

DETAILED DESCRIPTION OF THE INVENTION

According to a first aspect of the invention, there is provided a compound of formula (IB), or a salt, hydrate, solvate, single enantiomer or N-oxide thereof:

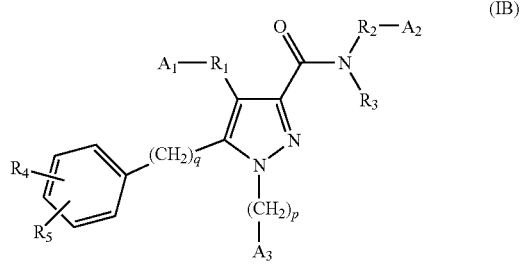

(IB)

WHEREIN:
$A_1$ is hydrogen, —COOH, or tetrazolyl;
p and q are independently 0 or 1;
$A_3$ is phenyl or cycloalkyl, either of which is optionally substituted with $R_4$ and/or $R_5$;
$R_4$ and $R_5$ independently —$R_9$, —CN, —F, —Cl, —Br, —$OR_9$, —$NR_7R_8$, —$NR_7COR_6$, —$NR_7SO_2R_6$, —$COR_6$, —$SR_9$, —$SOR_9$ or —$SO_2R_6$;
$R_6$ is $C_1$-$C_4$ alkyl, cycloalkyl, —$CF_3$ or —$NR_7R_8$;
$R_7$ and $R_8$ are independently hydrogen, $C_1$-$C_4$ alkyl or cycloalkyl;

$R_9$ is hydrogen, $C_1$-$C_4$ alkyl, $C_1$-$C_4$ alkoxy, $C_1$-$C_4$ alkoxy($C_1$-$C_4$ alkyl)-, cycloalkyl, fully or partially fluorinated $C_1$-$C_4$ alkyl;
$R_1$ is (i) a bond, or
(ii) —$(CH_2)_aB_1(CH_2)_b$— wherein a and b are independently 0, 1, 2 or 3 provided that a+b is not greater than 4, and $B_1$ is —CO—, —O—, —S—, —SO—, —$SO_2$—, —$CH_2$—, —CHOH— or —$NR_7$—; or
(iii) a divalent radical selected from —$C(R_{10})(R_{11})$—*, —$C(R_{10})(R_{11})$—O—*, —$C(R_{10})(R_{11})CH_2$—*, —$C(R_{10})(R_{11})CH_2$—O—*, —$CH_2C(R_{10})(R_{11})$—*, —$CH_2C(R_{10})(R_{11})$—O—*, —$CH_2$—O—$C(R_{10})(R_{11})$—* and —$C(R_{10})(R_{11})$—O—$CH_2$—*, wherein the bond indicated by an asterisk is attached to the pyrazole ring;
$R_{10}$ is hydrogen and $R_{11}$ is $(C_1$-$C_3)$alkyl; or $R_{10}$ and $R_{11}$ are both $(C_1$-$C_3)$alkyl; or $R_{10}$ and $R_{11}$ taken together with the carbon atom to which they are attached form a $(C_3$-$C_5)$cycloalkyl ring; and
the group —$N(R_3)R_2$-$A_2$ has formula (II), (III), (IV) or (V):

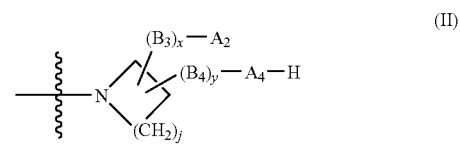

(II)

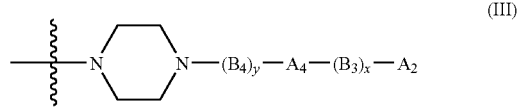

(III)

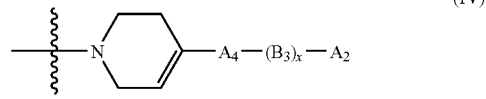

(IV)

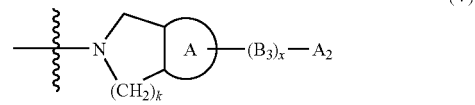

(V)

wherein x and y are independently 0 or 1, k is 1 or 2, and j is 1, 2, 3 or 4.
$B_3$ is —$C(R_{13})(R_{14})$—, —O—, or —$NR_7$—, or in either orientation —O—$C(R_{13})(R_{14})$—, —$CH_2$—$C(R_{13})(R_{14})$—;
$B_4$ is —$C(R_{13})(R_{14})$—, —CO—, —$SO_2$—, —O—, or in either orientation —O—$C(R_{13})(R_{14})$—, or —$CH_2$—$C(R_{13})(R_{14})$—.
$A_2$ is hydrogen, —COOH, tetrazolyl, —CN, —$CF_3$, —$COR_6$, —$SO_2R_6$, —$OR_9$, —$NR_7R_8$, —$NR_7COR_6$, or —$NR_7SO_2R_6$ provided that one of $A_1$ and $A_2$ is either —COOH or tetrazolyl;
$A_4$ is a monocyclic carbocyclic or monocyclic heterocyclic ring, having 3 to 8 ring atoms, optionally substituted with one or more of —F, —Cl, —Br, —CN, —$CF_3$, $C_1$-$C_4$ alkyl, cycloalkyl, —$OR_9$, oxo or —$NR_7R_8$;
Ring A is a fused monocyclic carbocyclic or monocyclic heterocyclic ring, having 3 to 8 ring atoms, optionally substituted with one or more of —F, —Cl, —Br, —CN, —$CF_3$, $C_1$-$C_4$ alkyl, cycloalkyl, —$OR_9$, oxo or —$NR_7R_8$; and
$R_{13}$ and $R_{14}$ are independently hydrogen or $(C_1$-$C_3)$alkyl; or $R_{13}$ and $R_{14}$ are both $(C_1$-$C_3)$alkyl; or $R_{13}$ and $R_{14}$ taken together with the carbon atom to which they are attached form a $(C_3$-$C_5)$cycloalkyl ring.

In compounds according to the above first aspect of the invention:

$R_9$ may be hydrogen, $C_1$-$C_4$ alkyl, cycloalkyl, fully or partially fluorinated $C_1$-$C_4$ alkyl; and $B_4$ may be —C($R_{13}$)($R_{14}$)—, —CO— or —SO$_2$—.

Thus the invention includes a compound of formula (I), or a salt, hydrate, solvate, single enantiomer or N-oxide thereof:

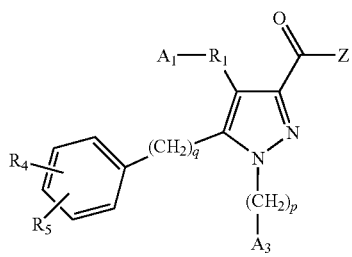
(I)

WHEREIN:

$A_1$ is hydrogen, —COOH, or tetrazolyl;

p and q are independently 0 or 1;

$A_3$ is phenyl or cycloalkyl, either of which is optionally substituted with $R_4$ and/or $R_5$;

$R_4$ and $R_5$ are independently —$R_9$, —CN, —F, —Cl, —Br, —$OR_9$, —$NR_7R_8$, —$NR_7COR_6$, —$NR_7SO_2R_6$, —$COR_6$, —$SR_9$, —$SOR_9$, or —$SO_2R_6$;

$R_6$ is $C_1$-$C_4$ alkyl, cycloalkyl, —$CF_3$ or —$NR_7R_8$;

$R_7$ and $R_8$ are independently hydrogen, $C_1$-$C_4$ alkyl or cycloalkyl;

$R_9$ is hydrogen, $C_1$-$C_4$ alkyl, $C_1$-$C_4$ alkoxy, $C_1$-$C_4$ alkoxy($C_1$-$C_4$ alkyl)-, cycloalkyl, or fully or partially fluorinated $C_1$-$C_4$ alkyl;

$R_1$ is (i) a bond;
(ii) a divalent radical of formula —(CH$_2$)$_a$B$_1$(CH$_2$)$_b$— wherein a and b are independently 0, 1, 2 or 3 provided that a+b is 1, 2 or 3, and $B_1$ is —CO—, —O—, —S—, —SO—, —SO$_2$—, —CH$_2$, —CHCH$_3$—, —CHOH— or —NR$_7$—; or
(iii) a divalent radical selected from —C($R_{10}$)($R_{11}$)—*, —C($R_{10}$)($R_{11}$)—O—*, —C($R_{10}$)($R_{11}$)CH$_2$—*, —C($R_{10}$)($R_{11}$)CH$_2$—O—*, —CH$_2$C($R_{10}$)($R_{11}$)—*, —CH$_2$C($R_{10}$)($R_{11}$)—O—*, —CH$_2$—O—C($R_{10}$)($R_{11}$)—* and —C($R_{10}$)($R_{11}$)—O—CH$_2$—*, wherein the bond indicated by an asterisk is attached to the pyrazole ring;

Z is selected from morpholin-1-yl and radicals of formula (II), (III), (IV), and (V)

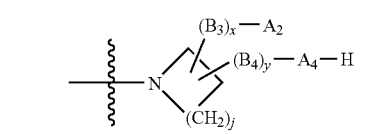
(II)

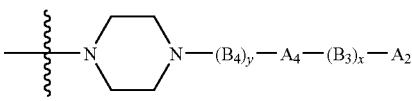
(III)

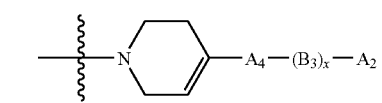
(IV)

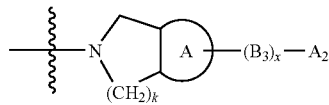
(V)

wherein
x and y are independently 0 or 1,
k is 1 or 2;
j is 1, 2, 3 or 4.

$A_2$ is hydrogen, —COOH, tetrazolyl, —CN, —CF$_3$, —COR$_6$, —SO$_2$R$_6$, —OR$_9$, —NR$_7$R$_8$, —NR$_7$COR$_6$, or —NR$_7$SO$_2$R$_6$ provided that when $A_1$ is hydrogen then $A_2$ is —COOH or tetrazolyl, $A_4$ is a bond or
(i) a monocyclic carbocyclic ring, having 3 to 8 ring atoms, optionally substituted with one or more of —F, —Cl, —Br, —CN, —CF$_3$, $C_1$-$C_4$ alkyl, cycloalkyl, —OR$_9$, oxo or —NR$_7$R$_3$ or SO$_2$R$_6$; or
(ii) a monocyclic heterocyclic ring, having 4 to 8 ring atoms, optionally substituted with one or more of —F, —Cl, —Br, —CN, —CF$_3$, $C_1$-$C_4$ alkyl, cycloalkyl, —OR$_9$, oxo or —NR$_7$R$_8$ or SO$_2$R$_6$, provided that for formula (IV), when $A_4$ is a bond, $B_3$ is not attached to $A_4$ by an oxygen or nitrogen $B_3$ is —C($R_{13}$)($R_{14}$)—, —O—, or —NR$_7$—, or in either orientation —O—C($R_{13}$)($R_{14}$)—, or —CH$_2$—C($R_{13}$)($R_{14}$)— provided that for formula (II)-(V), when x is 1 and $B_3$ is attached to $A_2$ by oxygen or nitrogen, then $A_2$ is hydrogen;

$B_4$ is —C($R_{13}$)($R_{14}$)—, —CO—, —SO$_2$—, —O—, or in either orientation —O—C($R_{13}$)($R_{14}$)—, or —CH$_2$—C($R_{13}$)($R_{14}$)—;

ring A is either:
(a) a fused monocyclic carbocyclic ring, having 3 to 8 ring atoms, optionally substituted with one or more of —F, —Cl, —Br, —CN, —CF$_3$, $C_1$-$C_4$ alkyl, cycloalkyl, —OR$_9$, oxo or —NR$_7$R$_8$; provided that when A is not aromatic and x is 1 and $B_3$ is attached to $A_2$ by oxygen or nitrogen, then $A_2$ is hydrogen; or
(b) a fused monocyclic heterocyclic ring, having 4 to 8 ring atoms, optionally substituted with one or more of —F, —Cl, —Br, —CN, —CF$_3$, $C_1$-$C_4$ alkyl, cycloalkyl, —OR$_9$, oxo or —NR$_7$R$_8$; provided that when A is not aromatic and x is 1 and $B_3$ is attached to $A_2$ by oxygen or nitrogen, then $A_2$ is hydrogen;

$R_{10}$ is hydrogen and $R_{11}$ is ($C_1$-$C_3$)alkyl or —OH; or $R_{10}$ and $R_{11}$ are both ($C_1$-$C_3$)alkyl; or $R_{10}$ and $R_{11}$ taken together with the carbon atom to which they are attached form a ($C_3$-$C_5$) cycloalkyl ring; and $R_{13}$ and $R_{14}$ are independently hydrogen or ($C_1$-$C_3$)alkyl; or $R_{13}$ and $R_{14}$ are both ($C_1$-$C_3$)alkyl; or $R_{13}$ and $R_{14}$ taken together with the carbon atom to which they are attached form a ($C_3$-$C_5$)cycloalkyl ring.

Another aspect of the invention is a pharmaceutical composition comprising a compound of formula (I) or a salt, hydrate, solvate or N-oxide thereof, together with one or more pharmaceutically acceptable carriers or excipients.

For orally administrable compounds with which the invention is concerned, it is preferable, according to known medicinal chemistry principles, to have a maximum compound molecular weight of 750, or even more preferably a maximum of 650

The compounds with which the invention is concerned suppress the normal signalling activity of cannabinoid receptor CB1. Therefore, further aspects of the invention are:

(i) The use of a compound of formula (I) or a salt, hydrate, solvate or N-oxide thereof in the preparation of a composition for treatment of diseases or conditions which are mediated by CB1 receptor signalling activity. Examples of such diseases have been listed above; and (ii) A method for the treatment of diseases or conditions which are mediated by CB1 receptor signalling activity, which method comprises administering to a subject suffering such disease or condition an effective amount of a compound of formula (I) or a salt, hydrate, solvate or N-oxide thereof. Again, examples of such treatments have been listed above.

Terminology

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, iso-propyl, n-butyl, isobutyl, sec-butyl, t-butyl, n-pentyl and n-hexyl.

As used herein the unqualified term "carbocyclic" refers to a mono-, bi- or tricyclic radical having up to 16 ring atoms, all of which are carbon, and includes aryl and cycloalkyl.

As used herein the unqualified term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, triazinyl, indolyl and indazolyl.

As used herein the unqualified term "heterocyclyl" or "heterocyclic" includes "heteroaryl" as defined above, and in addition means a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, $(C_1-C_6)$alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, halo (including fluoro, bromo and chloro), fully or partially fluorinated $(C_1-C_3)$alkyl, $(C_1-C_3)$alkoxy or $(C_1-C_3)$alkylthio such as trifluoromethyl, trifluoromethoxy, and trifluoromethylthio, nitro, nitrile (—CN), oxo, phenyl, phenoxy, monocyclic heteroaryl or heteroaryloxy with 5 or 6 ring atoms, tetrazolyl, —COOR$^A$, —COR$^A$, —OCOR$^A$, —SO$_2$R$^A$, —CONR$^A$R$^B$, —SO$_2$NR$^A$R$^B$, —NR$^A$R$^B$, OCONR$^A$R$^B$, —NR$^B$COR$^A$, —NR$^B$COOR$^A$, —NR$^B$SO$_2$OR$^A$ or —NR$^A$CONR$^A$R$^B$ wherein R$^A$ and R$^B$ are independently hydrogen or a $(C_1-C_6)$ alkyl group or, in the case where R$^A$ and R$^B$ are linked to the same N atom, R$^A$ and R$^B$ taken together with that nitrogen may form a cyclic amino ring, such as a morpholine, piperidinyl or piperazinyl ring. Where the substituent is phenyl, phenoxy or monocyclic heteroaryl or heteroaryloxy with 5 or 6 ring atoms, the phenyl or heteroaryl ring thereof may itself be substituted by any of the above substituents except phenyl, phenoxy, heteroaryl or heteroaryloxy. An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like.

For a review on suitable salts, see *Handbook of Pharmaceutical Salts: Properties, Selection, and Use* by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

So-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, 3$^{rd}$ Edition, 2002, Taylor and Francis).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985). Such examples could be a prodrug of a carboxyl group (such as —CO—O—CH$_2$—O—CO-tBu as used in the pivampicillin prodrug of ampicillin), an amide (—CO—NH—CH$_2$—NAlk$_2$) or an amidine (—C(=N—O—CH$_3$)—NH$_2$).

Also included within the scope of the invention are metabolites of compounds of formula (I), that is, compounds formed in vivo upon administration of the drug. Some examples of metabolites include (i) where the compound of formula I contains a methyl group, an hydroxymethyl derivative thereof (—CH$_3$→—CH$_2$OH);
(ii) where the compound of formula I contains an alkoxy group, an hydroxy derivative thereof (—OR→—OH);
(iii) where the compound of formula I contains a tertiary amino group, a secondary amino derivative thereof (—NR$^1$R$^2$→—NHR$^1$ or —NHR$^2$);
(iv) where the compound of formula I contains a secondary amino group, a primary derivative thereof (—NHR$^1$→—NH$_2$);
(v) where the compound of formula I contains a phenyl moiety, a phenol derivative thereof (-Ph→-PhOH); and
(vi) where the compound of formula I contains an amide group, a carboxylic acid derivative thereof (—CONH$_2$→COOH).

For use in accordance with the invention, the following structural characteristics are currently contemplated, in any compatible combination, in the compounds (I):

The Group A$_1$

A$_1$ is —COOH, or tetrazolyl.

The Group A$_3$

A$_3$ is phenyl or cycloalkyl such as cyclopentyl or cyclohexyl, optionally substituted with R$_4$ and/or R$_5$. Currently preferred is the case where A$_3$ is phenyl, optionally substituted with R$_4$ and/or R$_5$. Substituents R$_4$ and/or R$_5$ have been defined above, but currently preferred are cases where they are independently selected from hydrogen, —F, —CN and —Cl. When A$_3$ is phenyl or 6-membered heteroaryl, any R$_4$ and R$_5$ substituents in the phenyl ring shown in formula (I) as attached to —(CH$_2$)$_q$— and in A$_3$, will often be in the para and/or ortho positions of those rings. For example, in the phenyl ring shown in formula (I) as attached to —(CH$_2$)$_q$— R$_4$ may be hydrogen and R$_5$ is may be hydrogen and in the position para to —(CH$_2$)$_q$—, and separately or in combination with that feature, when A$_3$ is phenyl or 6-membered heteroaryl, in A$_3$ R$_4$ may be hydrogen and R$_5$ may be than hydrogen and in the position ortho to —(CH$_2$)$_p$—.

The Indices p and q

The indices p and q are independently 0 or 1, but currently preferred are cases where p and q are each 0.

The Divalent Radical R$_1$

R$_1$ has been defined above.

When not a bond, R$_1$ may be a divalent radical —(CH$_2$)$_a$B$_1$(CH$_2$)$_b$— as defined above. In such cases, B$_1$ may be, for example —CH$_2$— or —O—. Specific examples of radical R$_1$ include —CH$_2$—, —CH$_2$O—* wherein the bond marked with an asterisk is attached to the pyrazole ring, and —CH$_2$OCH$_2$—.

When not a bond, the radical R$_1$ may also be a divalent radical selected from —C(R$_{10}$)(R$_{11}$)—*, —C(R$_{10}$)(R$_{11}$)—O—*, —C(R$_{10}$)(R$_{11}$)CH$_2$—*, —C(R$_{10}$)(R$_{11}$)CH$_2$—O—*, —CH$_2$C(R$_{10}$)(R$_{11}$)—*, —CH$_2$C(R$_{10}$)(R$_{11}$)—O—*, —CH$_2$—O—C(R$_{10}$)(R$_{11}$)—* and —C(R$_{10}$)(R$_{11}$)—O—CH$_2$—*, wherein the bond indicated by an asterisk is attached to the pyrazole ring and wherein R$_{10}$ and R$_{11}$ are as defined above. In such radicals R$_{10}$ may be, for example, hydrogen or methyl, and R$_{11}$ may, for example, methyl. Specific examples of this type of radical R1 include —CH(OH)— and —CH(CH$_3$)—.

The Group Z

Z has been defined above.

In one currently preferred type of compound of the invention, Z has formula:

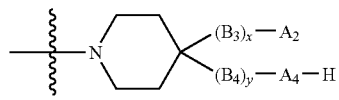

In another currently preferred type of compound of the invention, Z has formula:

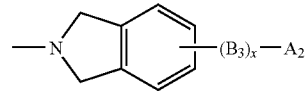

wherein the fused phenyl ring is optionally substituted with —F, —Cl, —Br, —CN, —CF$_3$, C$_1$-C$_4$ alkyl, cycloalkyl, —OR$_9$, oxo or —NR$_7$R$_8$.

When B$_3$ is present in the radical Z, B$_3$ may be, for example, —C(R$_{13}$)(R$_{14}$)—, or in either orientation —O—C(R$_{13}$)(R$_{14}$)—, —CH$_2$—C(R$_{13}$)(R$_{14}$)—, or —NR$_7$—, wherein R$_{13}$ and R$_{14}$ are independently hydrogen or methyl; and R$_7$ is hydrogen, methyl or cyclopropyl;

When B$_4$ is present in the radical Z, B$_4$ may be, for example, —C(R$_{13}$)(R$_{14}$)—, wherein R$_{13}$ and R$_{14}$ are independently hydrogen or methyl.

When A$_4$ is present in the radical Z, A$_4$ may be selected from, for example, the group consisting of phenyl, pyridine, pyrimidine, thiophene, furan, oxazole and thiazole rings.

The group A$_2$ in the radical Z may be, for example, —SO$_2$R$_6$, —OR$_9$, —NR$_7$R$_8$, —NR$_7$COR$_6$, or —NR$_7$SO$_2$R$_6$ then R$_6$ is selected from methyl or —CF$_3$; and R$_7$, R$_8$ and R$_9$ are independently selected from hydrogen or methyl.

In the radical Z in many embodiments of the invention, x and y are both 0 and A$_2$ is hydrogen, methyl, —CN, —OH, or —COOH.

Specific examples of the radical —C(=O)Z include those is selected from the group consisting of radicals of formulae (C)-(P):

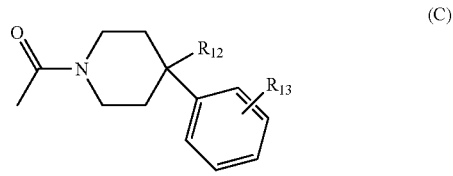

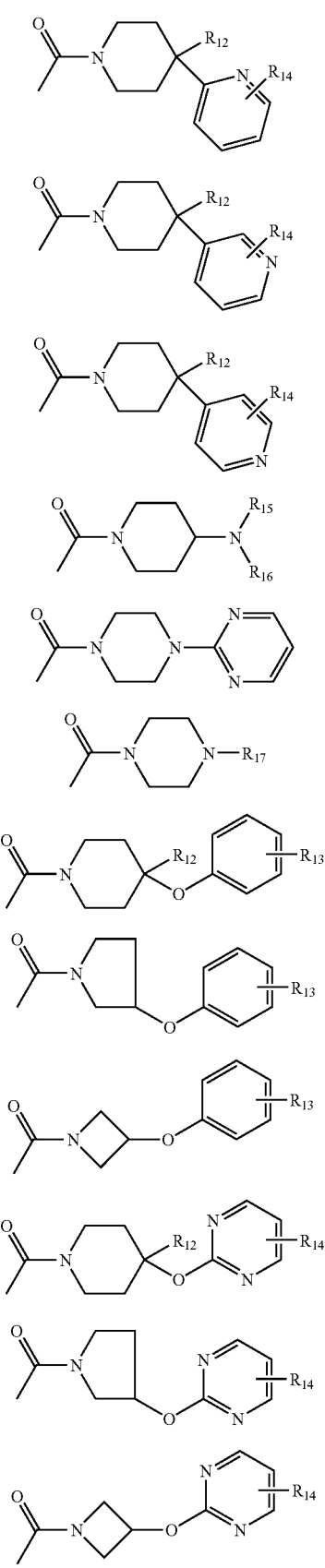

wherein (D) $R_{12}$ is selected from hydrogen, —$CH_3$, —OH, —CN and —COOH;
$R_{13}$ is selected from hydrogen, —F, —$CF_3$, —$OCF_3$, —Br, —Cl, —$OCH_3$, —$CH_3$, —CN and —COOH;
$R_{14}$ is selected from hydrogen, —F, —$CF_3$, —$OCF_3$, —Br, —Cl, —$OCH_3$, —CN, —OH, and —COOH;

(E) $R_{15}$ and $R_{16}$ are independently selected from hydrogen and ($C_1$-$C_6$)alkyl or $R_{15}$ and $R_{16}$ taken together with the nitrogen to which they are attached form a cyclic amino ring of 4 to 7 ring atoms;
$R_{17}$ is selected from hydrogen, ($C_1$-$C_6$)alkyl, ($C_1$-$C_6$)alkylC(=O)—, ($C_1$-$C_6$)alkyl$SO_2$—, benzyloxycarbonyl-, and —C(=O)$OCH_3$.

Currently preferred types of radical —C(=O)Z include those selected from the group consisting of:

(i) Formula D, wherein $R_{12}$ is hydrogen and $R_{14}$ is methyl, trifluoromethyl, trifluoromethoxy, 3-, 4- or 5-fluoro, 3-, 4- or 5-chloro, or 3-, 4- or 5-cyano, or 6-hydroxy;

(ii) Formula E, wherein $R_{12}$ is hydrogen and $R_{14}$ is methyl, trifluoromethyl, 4- or 5-fluoro, 4- or 5-chloro, or, 4- or 5-cyano, or 2-, 6-hydroxy;

(iii) Formula H;

(iv) Formula (C) or any of (K)-(P), wherein $R_{12}$ is hydrogen and $R_{13}$ or $R_{14}$ is F, Cl, trifluoromethyl, trifluoromethoxy, cyano, methylsulfonyl Currently particularly preferred types of radical —C(=O)Z have Formula C, wherein $R_{12}$ is hydroxyl, cyano or —COOH, and $R_{13}$ is fluoro, methyl, trifluoromethyl, cyano, or methoxy.

With reference to formulae (C)-(P), any substituents in a heteroaromatic ring must of course be consistent with known medicinal chemistry principles. For example, it is unlikely that any substitutent halogen or CN in a nitrogen-containing heteroaromatic ring will be adjacent to the nitrogen atom, since such substituent is expected to behave as a good leaving group, implying that in vivo such compounds would have a strong potential to react with nucleophilic entities, leading to covalent bond formation, generally regarded as undesirable for potential toxicicty reasons. Also for example, it is likely that any OH substituent will be adjacent to the nitrogen atom since again such compounds can lead to potential toxicity.

A specific subset of compounds of the invention consists of those of formula (IA) or a salt, hydrate, solvate, single enantiomer or N-oxide thereof:

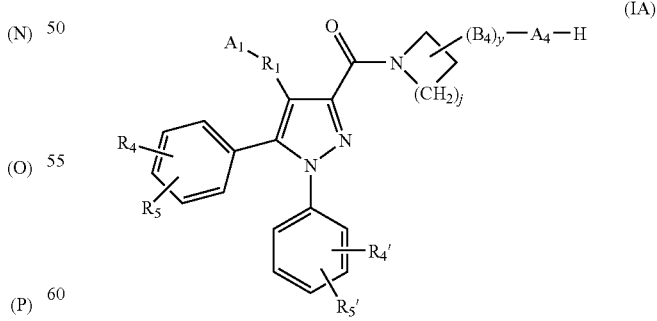

(IA)

wherein
$A_1$ is —COOH, or tetrazolyl;
—$R_1$— is —$CH_2$—, —CH(OH)—, —$CHCH_3$—, —$CH_2O$—* wherein the bond indicated by an asterisk is attached to $A_1$ $R_4$, $R_5$, $R_4'$ and $R_5'$ are independently selected from hydrogen, —F, —CN and —Cl;

j is 1, 2 or 3 y is either 0 or 1

$B_4$ is —C($R_{13}$)($R_{14}$)—, —CO—, —SO$_2$—, —O—, or in either orientation —O—C($R_{13}$)($R_{14}$)—, or —CH$_2$—C($R_{13}$)($R_{14}$)—;

$A_4$ is (i) a monocyclic carbocyclic ring, having 3 to 8 ring atoms, optionally substituted with one or more of —F, —Cl, —Br, —CN, —CF$_3$, $C_1$-$C_4$ alkyl, cycloalkyl, —OR$_9$, oxo or —NR$_7$R$_8$ or SO$_2$R$_6$, or (ii) a monocyclic heterocyclic ring, having 4 to 8 ring atoms, optionally substituted with one or more of —F, —Cl, —Br, —CN, —CF$_3$, $C_1$-$C_4$ alkyl, cycloalkyl, —OR$_9$, oxo or —NR$_7$R$_8$ or SO$_2$R$_6$.

In compounds (IA), $R_4$ may be, for example, hydrogen and $R_5$ may be other than hydrogen and in the para position. Separately or in combination with that feature. In compounds (IA), $R_4'$ may be, for example, hydrogen and $R_5'$ may be other than hydrogen and in the ortho position.

Specific compounds of the invention include those of the Examples herein.

The compounds of the present invention act on central and peripheral cannabinoid receptor CB1. Some compounds distribute to a lesser extent to the central nervous system, i.e. the compound less readily crosses the blood-brain barrier and will be associated with fewer central nervous system mediated side-effects.

The compounds of the invention modulate the cannabinoid receptor CB1 by suppressing its natural signalling function. The compounds are therefore CB1 receptor antagonists, inverse agonists, or partial agonists.

The term "CB1 antagonist" or "cannabinoid receptor CB1 antagonist" refers to a compound which binds to the receptor, or in its vicinity, and lacks any substantial ability to activate the receptor itself. A CB1 antagonist can thereby prevent or reduce the functional activation or occupation of the receptor by a CB1 agonist such as for example the endogenous agonist N-Arachidonylethanolamine (anandamide). This term is well known in the art.

The term "CB1 inverse agonist" or "cannabinoid receptor CB1 inverse agonist" refers to a compound which binds to the receptor and exerts the opposite pharmacological effect as a CB1 receptor agonist does. Inverse agonists are effective against certain types of receptors which have intrinsic activity without the acting of a ligand upon them (also referred to as 'constitutive activity'). This term is well known in the art. It is also well known in the art that such a CB1 inverse agonist can also be named a CB1 antagonist as the general properties of both types are equivalent. Accordingly, in the context of the present invention the term "CB1 antagonist" in general is understood as including both the "CB1 antagonist" as defined above and the "CB1 inverse agonist".

The term "CB1 partial agonist" or "cannabinoid receptor CB1 partial agonist" refers to a compound which acts upon the same receptor as the full agonist but that produces a weak maximum pharmacological response and has a low level of intrinsic activity. This term is well known in the art.

According to a preferred embodiment of the present invention, the "CB1 modulator" or "cannabinoid receptor CB1 modulator" is a CB1 antagonist or inverse agonist compound.

The compounds of the invention are useful for the treatment of diseases or conditions which are mediated by CB1 receptor signalling activity. Examples of such diseases and conditions and treatments therefor have been listed above. Without limitation, they include obesity and overweight, prevention of weight gain, treatment of diseases and conditions directly or indirectly associated with obesity (e.g. metabolic syndrome, type 2 diabetes, cardiovascular diseases, metabolic dysfunctions in obese, overweight or normoweight individuals, metabolic diseases or disorders, cancers, liver diseases and the other secondary diseases referred to above), and in the treatment of diseases and conditions not necessarily related to obesity (e.g. eating disorders, addictive disorders, mental disorders, neurological disorders, sexual dysfunctions, reproductive dysfunctions, liver diseases, fibrosis-related diseases and other clinical indications referred to above). They are useful for modulating body weight and energy consumption in mammals and for modulating major components involved in the metabolic syndrome such as excess abdominal fat, atherogenic dyslipidemia (abnormal levels of HDL-C, triglycerides, LDL, apolipoprotein B, adiponectin), hypertension, hyperglycaemia, hyperuricaemia, non-alcoholic fatty liver disease/hepatic steatosis, elevated liver transaminases, gamma-glutamyl-transferase and microalbuminuria. The compounds of the invention display varying physicochemical properties and are useful for modulating peripheral CB1 receptors and to varying degree central CB1 receptors. Those compounds of the invention associated with a lowered central action on CB1 receptors may have a reduced propensity to induce psychiatric and nervous system side-effects.

The compounds of the invention may be combined with another therapeutic agent used in treatment of obesity acting by a different mode of action such as central action on satiety or hunger signals, craving mechanisms, appetite regulation, leptin/insulin/central nervous system pathways, gastrointestinal-neural pathways, metabolic rate, energy expenditure, food intake, fat storage, fat excretion, gastrointestinal motility, lipogenesis, glucose transport, glucogenolysis, glycolysis, lipolysis, etc including modulators (inhibitors, agonists, antagonists, analogues) of monoaminergic (NA (noradrenaline), 5-HT (serotonin), DA (dopamine)) receptors or transporters, neural ion channels, leptin or leptin receptor, neuropeptide Y receptors, PP (pancreatic polypeptide), PYY, Protein YY3-36, ghrelin or ghrelin receptor, motilin or motilin receptor, orexins or orexin receptors, bombesin or bombesin-like peptide receptors, somatostatin or somatostatin receptors, MCHR1 (melanin concentrating hormone receptor 1), CNTF (ciliary neurotrophic factor), AgRP (agouti-related peptide), POMC (proopiomelanocortin), CART (cocaine and amphetamine regulated transcript), alpha-MSH (alpha-melanocyte-stimulating hormone), MC4 (melanocortin-4) or MC3 (melanocortin-3) receptor, galanin receptors, relaxin-3 receptor, GPR7 receptor, GPR119 receptor, GPR10 receptor, neuromedin U receptors, free-fatty-acid receptors, growth hormone, nesfatin-1, opioid receptors, neuropeptide FF receptors, PTP-1B (protein-tyrosine phosphatase), PPAR (peroxisome proliferators activated receptors) receptors, retinoid X receptor heterodimers, adiponectin also known as Acrp30 (adipocyte complement-related protein of 30 kDa), fatty acid metabolism, H (histamine) receptors, CCK-A (Cholecystokinin-A) or CCK-A receptor, GLP-1 (glucagon-like peptide-1) or GLP-1 receptor, oxyntomodulin, adrenomedullin, DPP-IV (dipeptidyl peptidase IV), amylin, beta-3-adrenergic receptor, UCP (uncoupling protein), thyroid receptor, thyroid-stimulating hormone receptor, 11beta-hydroxysteroid dehydrogenase type 1, amylase, DHEAS (dehydroepiandrosterone sulfate), CRH (corticotropin releasing hormone) or CRH receptors, carboxypeptidase, fatty acid synthesis, HMG-CoA reductase, ileal bile acid transport, gastrointestinal lipase, P57, AMP-activated protein kinase (AMPK).

The compounds of the invention may be combined with another therapeutic agent used in treatment of metabolic syndrome or obesity-related diseases such as cardiovascular (hypertension, congestive cardiomyopathy, varicosities, pulmonary embolism, coronary heart disease [CHD], liver cirrhosis), neurological (stroke, idiopathic intracranial hypertension, meralgia parethetica), respiratory (dyspnea, obstructive sleep apnea, hypoventilation syndrome, Pickwickian syndrome, asthma), musculoskeletal (immobility, degenerative osteoarthritis, low back pain, osteoporosis), skin (striae distensae or "stretch marks," venous stasis of the lower extremities, lymphedema, cellulitis, intertrigo, carbuncles, acanthosis nigricans, skin tags), gastrointestinal (gastroesophageal reflux disorder, nonalcoholic fatty liver/steatohepatitis, cholelithiasis, hernias, colon cancer), genitourinary (stress incontinence, obesity-related glomerulopathy, breast and uterine cancer), psychological (depression and low self-esteem, impaired quality of life), and endocrine (metabolic syndrome, type 2 diabetes, dyslipidemia, hyperandrogenemia in women, polycystic ovarian syndrome, dysmenorrhea, infertility, pregnancy complications, male hypogonadism) diseases.

The compounds of the invention may be combined with proper reduction in dietary calorie intake and physical exercise.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. However, for administration to human patients, the total daily dose of the compounds of the invention may typically be in the range 1 mg to 1000 mg depending, of course, on the mode of administration. For example, oral administration may require a total daily dose of from 10 mg to 1000 mg, while an intravenous dose may only require from 1 mg to 500 mg. The total daily dose may be administered in single or divided doses and may, at the physician's discretion, fall outside of the typical range given herein.

These dosages are based on an average human subject having a weight of about 60 kg to 100 kg. The physician will readily be able to determine doses for subjects whose weight falls outside this range, such as infants and the elderly, and especially obese patients.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "*Advanced organic chemistry*", 4$^{th}$ Edition (Wiley), J March, "*Comprehensive Organic Transformation*", 2$^{nd}$ Edition (Wiley), R. C. Larock, "*Handbook of Heterocyclic Chemistry*", 2$^{nd}$ Edition (Pergamon), A. R. Katritzky), P. G. M. Wuts and T. W. Greene "Greene's Protective Groups in Organic Chemistry" 4$^{th}$ Edition (Wiley) review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*".

General Synthetic Routes

Routes outlined below do not constitute an exhaustive list.

Experimental conditions given are generic and can be found in standard literature sources such as those cited above. Specific references are cited for information and conditions may apply to a given substrate with or without modification/optimization.

The compounds of Formula I may be obtained by introduction of the —N(R$_3$)R$_2$-A$_2$ moiety to a corresponding carboxylic acid or a protected form of the depicted carboxylic acid as outlined in the following scheme:

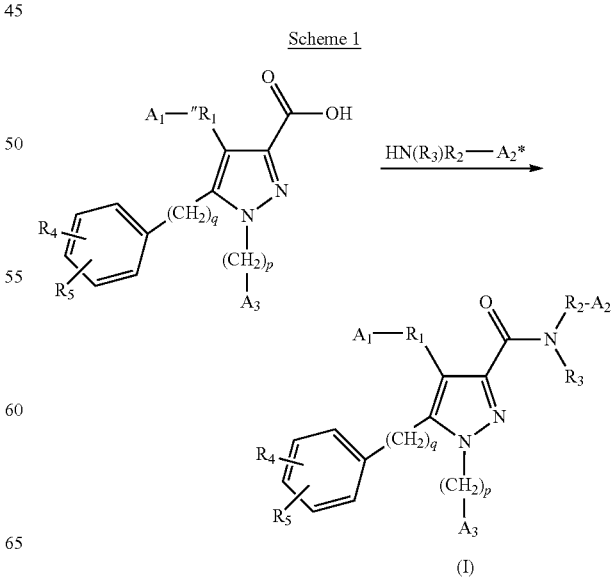

Thus, the HN(R₃)R₂-A₂* moiety contains a nucleophilic nitrogen center and the remaining part could include the final substituent, a protected version of the substituent (e.g. an ester) or a group which can be converted to the final substituent using standard procedures known to those skilled in the art (e.g. conversion of nitrile to tetrazole). Thus, compounds of Formula I may either be obtained directly following the procedure in scheme 1 or after standard conversions such as removal of protecting groups.

The carboxylic acids can be in activated forms (e.g. acid chlorides or active esters) or alternatively the conversion can be made directly from the acid using suitable coupling reagents such as dicyclohexylcarbodiimide (DCC), and promoters such as 1-hydroxybenzotriazole (HOBT).

Compounds of Formula (I) can also be obtained by following a related procedure to that described above whereupon a carboxylic acid derivative (e.g. nitrile, ester or amide), or other suitable precursor is converted into the group $A_1$ after the amide formation. For instance as outlined in the following scheme:

Scheme 2

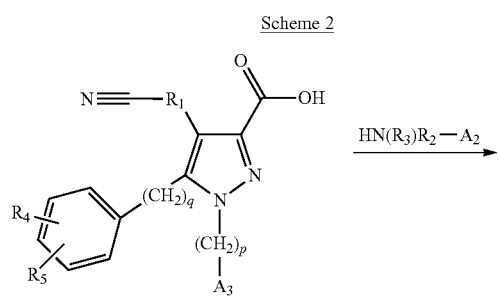

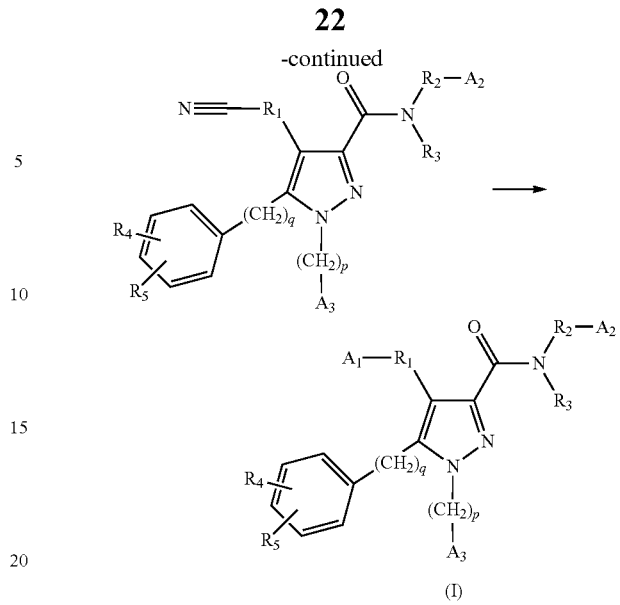

Such a procedure may include for instance conversion of a nitrile group to a tetrazole under standard conditions (e.g. by treatment with sodium azide and a weak acid such as dimethylamine hydrochloride in a polar solvent such as DMF) or the conversion of a nitrile group to a carboxylic acid. This latter conversion may either be achieved directly (e.g. by hydrolysis under acidic or basic conditions) or in a two step process involving initial formation of an ester or imidate (e.g. by treatment with an alcohol and anhydrous hydrogen chloride) followed by hydrolysis under standard conditions (e.g. with aqueous sodium hydroxide).

An alternative strategy for the preparation of compounds of formula (1) could be by introduction of the $A_1$ moiety via alkylation of a suitable nucleophilic center. Thus possible procedures could include those outlined in the following scheme:

Scheme 3

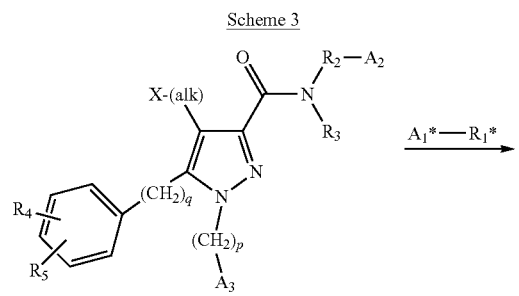

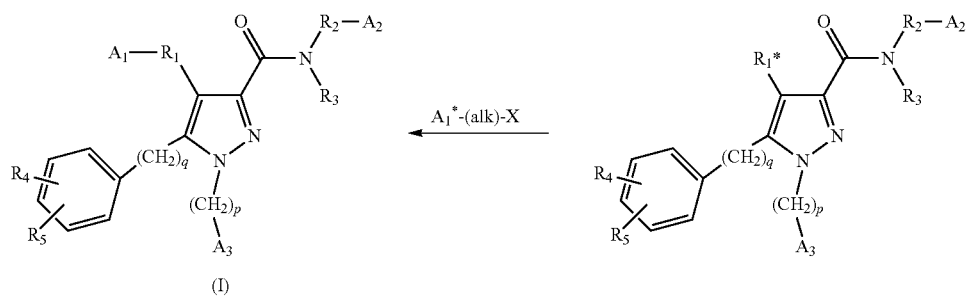

Thus the $R_1^*$ moiety contains a nucleophilic oxygen, sulphur, nitrogen or carbon, X represents an appropriate leaving group (e.g. bromo) and the group $A_1^*$ could either represent the final substituent or a precursor to the final substituent such as a nitrile or ester group.

The above procedures are applicable to the synthesis of compounds of formula (1) whereby either one or more of the radicals $R_1$, $R_2$ and $R_3$ include a branched chain or where $R_2$ and $R_3$ together form a ring. Alternatively these compounds may be obtained from a related unbranched derivative of formula (1) or precursor to this. For instance reaction of one or more of the moieties $R_1$, $R_2$ or $R_3$ in appropriately activated positions with an alkylating agent (e.g. iodomethane). For example compounds of formula (1) could be obtained by alkylation alpha- to a nitrile group such as in the following scheme:

Scheme 4

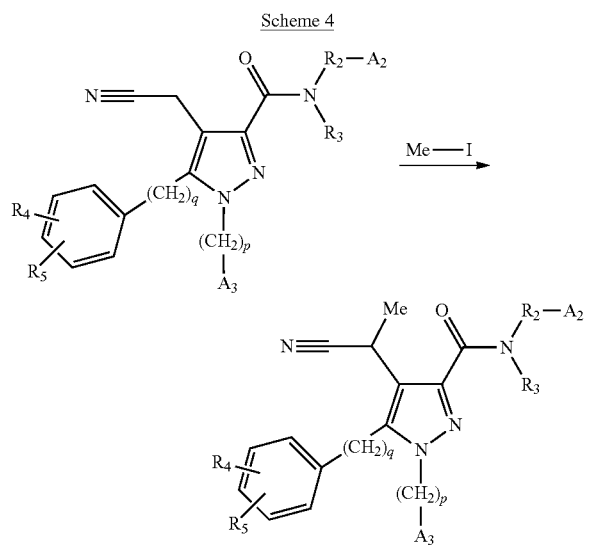

This conversion could for instance be accomplished by using a strong base such as lithium diisopropylamide (LDA), in an aprotic solvent (e.g. THF) and in the presence of suitable cofactors (e.g. TMEDA) according to procedures well known to those skilled in the art. Compounds of formula (1) could hence be obtained by conversion of the nitrile group to a tetrazole or carboxylic acid following previously described procedures.

Alternatively, compounds of formula (1) may be obtained from other compounds of formula (1) by functional group interconversion as the final step. For instance, the substituents $R_4$ and $R_5$ can be introduced at a final stage in the phenyl ring or the $A_3$ moiety as exemplified in the following scheme:

Scheme 5

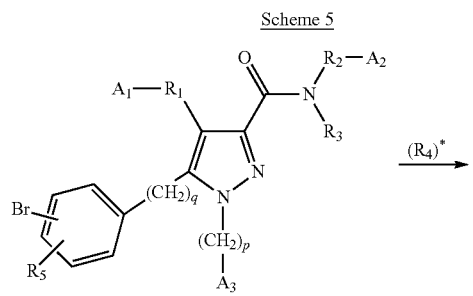

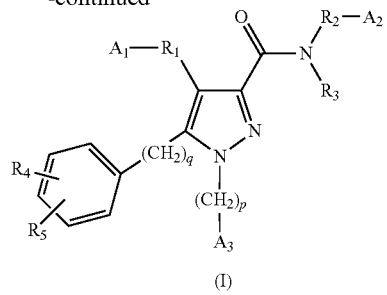

(I)

For example, this may involve reacting a bromo compound with zinc cyanide in the presence of a metal catalyst such as a palladium(0) complex, to give a compound of formula (1) where $R_4$ is cyano.

Such a conversion may also be made on an intermediate that can be converted to the compounds of Formula I or on a protected version of the intermediates. Analogously, substituents may also be introduced in the $R_2$ moiety at the final stage of the reaction sequence.

The reactants used in the above schemes may either be described in the literature or obtained by following analogous procedures to those described in the literature, in some cases followed by simple functional group conversions familiar to those skilled in the art.

The experimental section contains examples of the different synthetic routes and the person skilled in the art may apply analogous routes using procedures found in the literature to make compounds represented by Formula I.

Analysis:

$^1$H NMR resonances were measured on a Bruker Avance AMX 300 MHz spectrometer and chemical shifts are quoted for selected compounds in parts-per-million (ppm) downfield relative to tetramethylsilane as internal standard.

LCMS analysis was obtained under standardised conditions as follows:

Column; Gemini C18, 5 µm, 2.0×50 mm. Flow: 1.2 ml/min; Gradient: Acetonitrile in 0.1% aqueous trifluoroacetic acid: 10%-95% acetonitrile over 3.5 minutes then 95% acetonitrile for 1.0 minute. Instrument: Agilent 1100 HPLC/MSD system, 254 nm UV detection. MS-ionisation mode: API-ES (pos. or neg.).

Data is quoted for all compounds as retention time (RT) and molecular ion $(M+H)^+$ or $(M-H)^-$:

UPLC/MS was performed on a Waters Acquity—under standardised conditions as follows Column: ACQUITY UPLC BEH 018, 1.7 µm, 2.1×50 mm. Flow: 0.5 ml/min. Gradient: 0.1-1.0 min: 24-94% acetonitrile in water, 1-1.8 min: 94% acetonitrile. Modifier: 0.1% HCOOH. MS-ionisation mode: API-ES (pos. and neg. ionization)

Preparative HPLC:

This was performed with mass-directed fraction collection under standardised conditions as follows:

Column: YMC 19×100 mm; Flow: 20 mL/min. Gradient: 0-8 min: 10-70% MeCN in water, 8-9 min: 70-95% MeCN in water, 9-12 min: 95% MeCN. Modifier: 0.1% TFA; MS-ionisation mode: API-ES (pos.)

Synthesis of Intermediates:

Intermediates of formula [A], [B] and [C] were prepared as described in the following scheme:

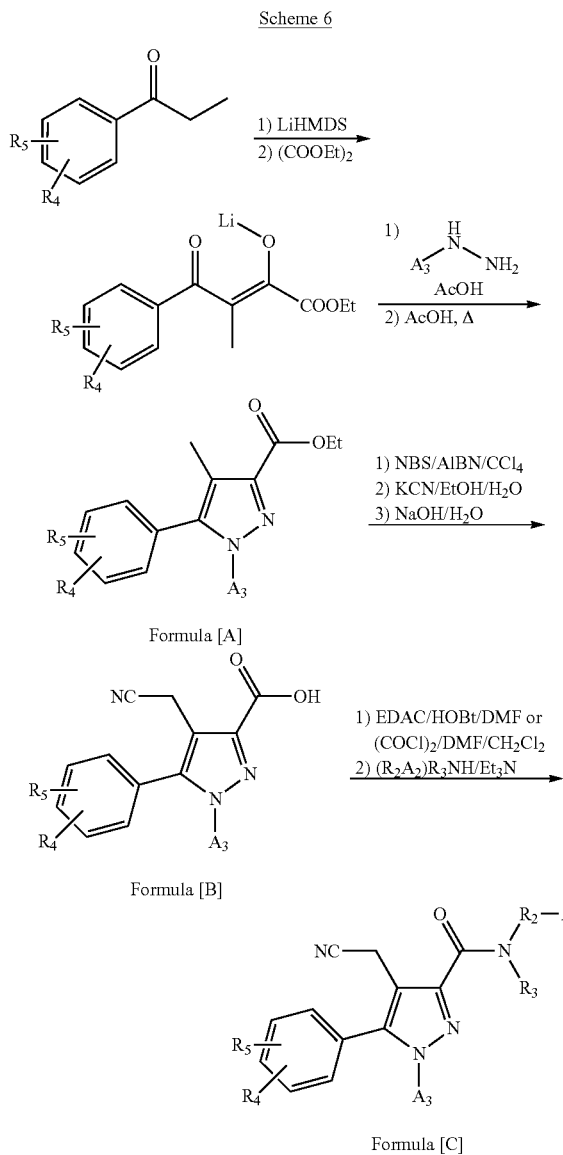

Pyrazole derivatives of formula [A] may be obtained by well known methods (J. Med. Chem, 1999, 42, 769-776).

Intermediates of formula [B] were obtained from compounds of formula [A] by bromination with N-bromosuccinimide (NBS) in the presence of catalytic 2,2'-azobisisobutyronitrile (AIBN) in tetrachloromethane, followed by reaction with potassium cyanide in aqueous ethanol then ester hydrolysis with aqueous sodium hydroxide.

Intermediates of formula [C] were obtained from the respective intermediates of formula [B] and amines $R^3R^4NH$ by coupling either using 1-(3-dimethylaminopropyl)-3-ethylcarbodiimide hydrochloride (EDAC) and 1-hydroxybenzotriazole (HOBT) or by pre-formation of the acid chloride with oxalyl chloride and catalytic N,N-dimethylformamide (DMF).

Intermediates of formula [D] and [E] were prepared as described in the following scheme:

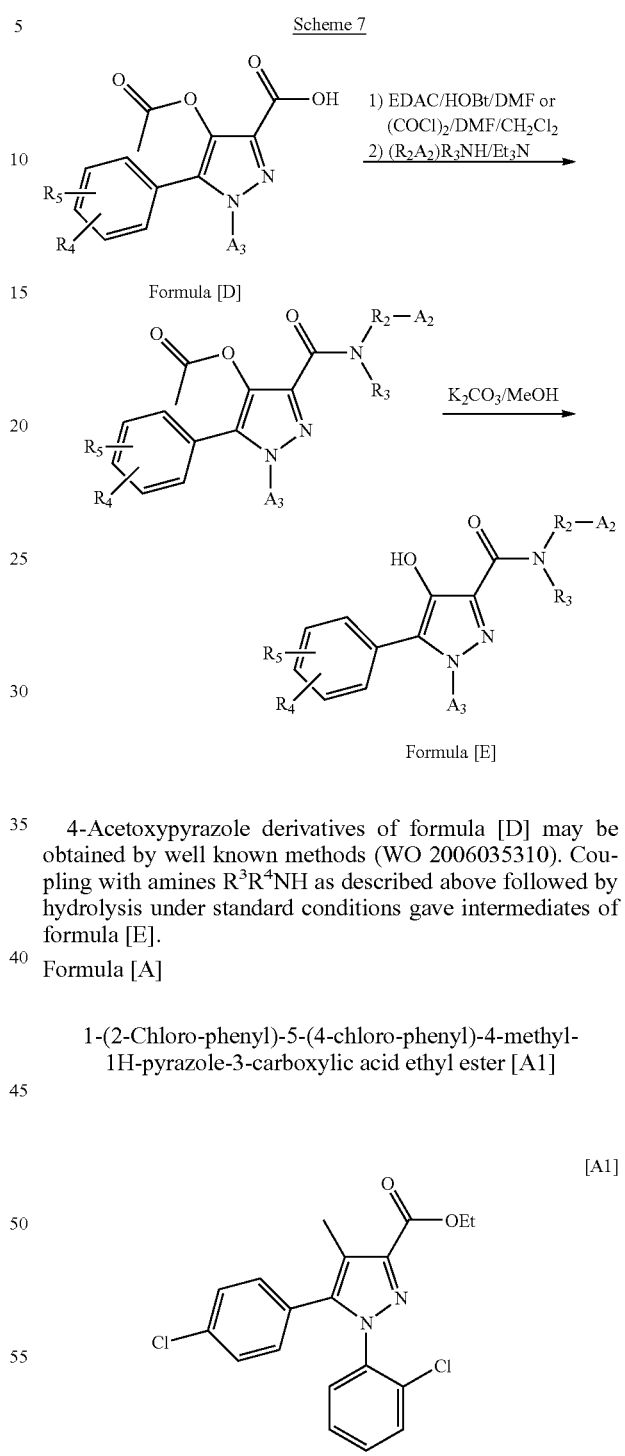

4-Acetoxypyrazole derivatives of formula [D] may be obtained by well known methods (WO 2006035310). Coupling with amines $R^3R^4NH$ as described above followed by hydrolysis under standard conditions gave intermediates of formula [E].

Formula [A]

1-(2-Chloro-phenyl)-5-(4-chloro-phenyl)-4-methyl-1H-pyrazole-3-carboxylic acid ethyl ester [A1]

A solution of 4'-chloropropiophenone (33.7 g, 200 mmol) in heptane (340 ml) was added to a stirred solution of lithium bis(trimethylsilyl)amide (1M in hexanes, 240 ml, 240 mol) under nitrogen at such a rate that the internal temperature did not exceed 25° C. After 2 hours, diethyloxalate (29.9 ml, 220 mmol) was added and the mixture was stirred for a further 16 hours at 25° C.

The resulting solid was filtered, washed with heptane and partially dried in vacuo to give (Z)-4-(4-chloro-phenyl)-2-hydroxy-3-methyl-4-oxo-but-2-enoic acid ethyl ester lithium salt (76 g) as a solid (76 g)

This solid (38 g) was dissolved in acetic acid (350 ml) and 2-chlorophenylhydrazine hydrochloride (16.11 g, 90 mmol) was added. The mixture was stirred at room temperature for 3 h then poured into water (680 ml), stirred for 2 h then the resulting solid collected by filtration and partially dried by suction. The solid was dissolved in acetic acid (230 ml) and the solution heated to reflux for 18 hours, cooled to room temp and poured into water (600 ml). After stirring for 24 h, the resulting precipitate was collected by filtration, washed with water then purified by recrystallisation from 2-propanol/water. The resulting solid was dried in vacuo at 50° C. to give the title compound [A1] (16.1 g, 48%).

1H NMR (CDCl$_3$): δ 1.44 (3H, t), 2.36 (3H, s), 4.48 (2H, q), 7.09-7.12 (2H, m), 7.28-7.35 (6H, m).
LCMS: RT=3.3 min, (M+H)$^+$=375.
Formula [B]

5-(4-Chloro-phenyl)-1-(2-chloro-phenyl)-4-cyanomethyl-1H-pyrazole-3-carboxylic acid [B1]

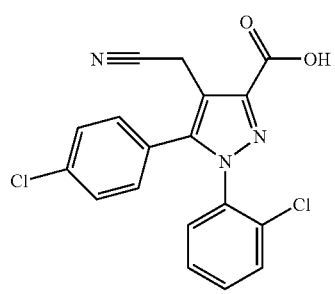

2,2'-Azobisisobutyronitrile (0.35 g, 2.13 mmol) was added to a stirred solution of [A1] (16 g, 42.6 mmol) and N-bromosuccinimide (8.35 g, 46.9 mmol) in tetrachloromethane (160 ml) and the mixture heated to reflux for 2 hours then cooled to room temperature. Saturated aqueous sodium metabisulphite solution (30 ml) was added and the mixture stirred for 24 hours then diluted with water (160 ml) plus brine (40 ml) and extracted with ethyl acetate (240 ml). The organic extracts were extracted with 1M sodium hydroxide solution (100 ml), dried over anhydrous magnesium sulphate and evaporated in vacuo.

The residue was dissolved in ethanol (100 ml) and a solution of potassium cyanide (8.33 g, 127.8 mmol) in water (25 ml) added. The mixture heated at reflux for 16 hours. 2M Sodium hydroxide solution (20 ml) was added and reflux continued for 30 minutes.

The mixture was diluted with water (300 ml), acidified with 2M hydrochloric acid and extracted with ethyl acetate (2×300 ml). Combined organic extracts were dried over magnesium sulphate and filtered through a silica pad, washing initially with ethyl acetate then 1% acetic acid in ethyl acetate. The filtrate was evaporated in vacuo then the residue co-evaporated with toluene to remove acetic acid and give the title compound [B1] (14.7 g, 93%) as a foam.

$^1$H NMR (DMSO-D$_6$): δ 3.91 (2H, s), 7.10 (2H, d), 7.23-7.37 (6H, m).
LCMS: RT=2.476 min, (M+H)$^+$=372.
Formula [C1]

[5-(4-Chloro-phenyl)-1-(2-chloro-phenyl)-3-(4-phenyl-piperazine-1-carbonyl)-1H-pyrazol-4-yl]-acetonitrile [C1]

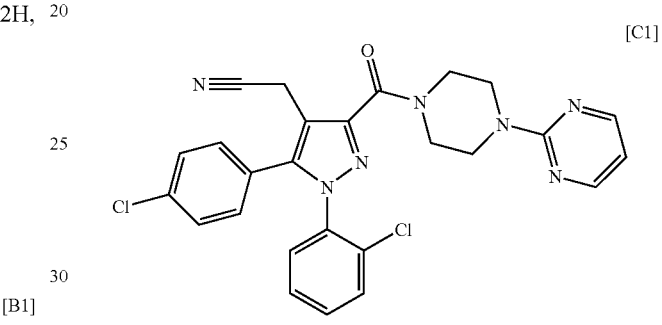

EDAC (195 mg, 1.00 mmol) was added to a stirred solution of [B1] (250 mg, 0.7 mmol) and HOBT (133 mg, 0.8 mmol) in dichloromethane (40 ml) at room temperature under argon. After 15 minutes 2-(piperazinyl)pyrimidine (155 mg, 0.9 mmol) was added and stirring continued for 16 hours. The mixture was washed with saturated aqueous sodium bicarbonate solution (3×) then with brine, dried over magnesium sulphate, filtered and evaporated in vacuo to give the crude, which was purified by preparative chromatography to give 9 mg of [C1].

LCMS: RT=3.450 min. (M+H)$^+$=519.0

The following intermediates of formula [C] were also prepared from [B1] and the respective amines, following an analogous procedure to that described above:

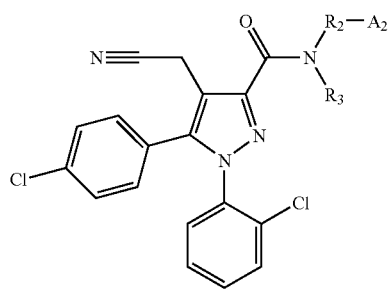

| Compound Number | Compound Name | 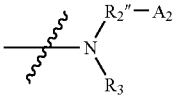 | LCMS |
|---|---|---|---|
| [C2] | [5-(4-Chloro-phenyl)-1-(2-chloro-phenyl)-3-(4-hydroxy-4-phenyl-piperidine-1-carbonyl)-1H-pyrazol-4-yl]-acetonitrile. | 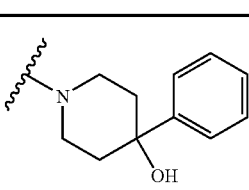 | RT = 2.8 min. (M + H)$^+$ = 513.2 |
| [C3] | [5-(4-Chloro-phenyl)-1-(2-chloro-phenyl)-3-(5-fluoro-1,3-dihydro-isoindole-2-carbonyl)-1H-pyrazol-4-yl]-acetonitrile | 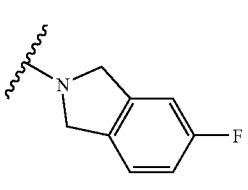 | RT = 3.2 min. [M + H]$^+$ = 491.0 |
| [C4] | [5-(4-Chloro-phenyl)-1-(2-chloro-phenyl)-3-[4-(4-fluoro-phenyl)-piperidine-1-carbonyl]-1H-pyrazol-4-yl]-acetonitrile. | 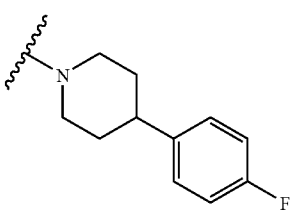 | RT = 3.3 min. [M + H]$^+$ = 533.0 |
| [C5] | [5-(4-Chloro-phenyl)-1-(2-chloro-phenyl)-3-[4-(2-fluoro-phenyl)-piperidine-1-carbonyl]-1H-pyrazol-4-yl]-acetonitrile. | 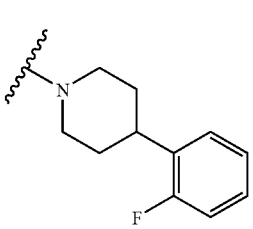 | RT = 3.4 min. [M + H]$^+$ = 533.0 |

Formula [D]

4-Acetoxy-5-(4-chloro-phenyl)-1-(2-chloro-phenyl)-1H-pyrazole-3-carboxylic acid [D1]

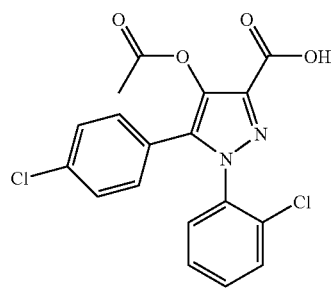

Prepared according to the published procedure (WO 2006035310).

$^1$H NMR (DMSO-D$_6$): δ 2.27 (3H, s), 7.20 (2H, d), 7.44 (2H, d), 7.59 (3H, m), 7.80 (1H, d), 13.28 (1H, s, br).

Formula [E]

5-(4-Chloro-phenyl)-1-(2-chloro-phenyl)-4-hydroxy-1H-pyrazole-3-carboxylic acid 4-fluoro-phenylpiperidine amide [E1]

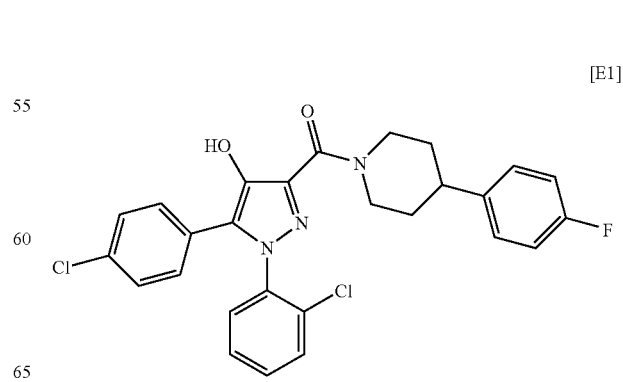

The acid [D1] and 4-fluorophenylpiperidine were coupled according to the procedure outlined above for the preparation of [C1] to give acetic acid 5-(4-chloro-phenyl)-1-(2-chloro-phenyl)-3-(4-fluoro-benzylcarbamoyl)-1H-pyrazol-4-yl ester.

This ester (95 mg, 0.17 mmol) was dissolved in hot methanol. Potassium carbonate (26 mg, 0.19 mmol) was added in one portion to give a clear pale-yellow solution which was stirred for 1 hour at room temperature. The reaction mixture was acidified with 1M hydrochloric acid, diluted with water and extracted twice with dichloromethane. The organic phases were combined, dried over anhydrous magnesium sulphate, filtered and evaporated in vacuo to give the title compound [E1] (85 mg, 96%). as a pale yellow solid LCMS: RT=3.9 min. (M+H)$^+$=510.1

Compounds of General Formula [1]

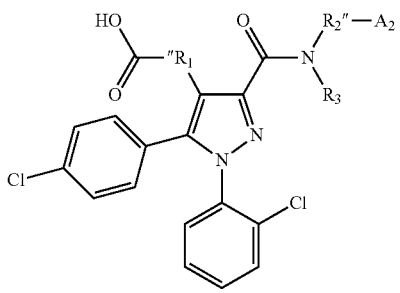

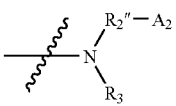

| Compound Number | Compound Name | ![structure](N-R2''-A2, R3) | R1 | Analysis LCMS/1H NMR |
|---|---|---|---|---|
| [1.5] | {5-(4-Chloro-phenyl)-1-(2-chloro-phenyl)-3-[4-(4-fluoro-phenyl)-piperidine-1-carbonyl]-1H-pyrazol-4-yl}-acetic acid | 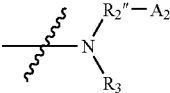 | —CH$_2$— | RT = 3.2 min [M + H]$^+$ = 552<br>$^1$H 300 MHz., DMSO: δ 12.45 (1H, bs), 7.64-7.54 (2H, m), 7.53-7.39 (4H, m), 7.33-7.20 (4H, m), 7.16-7.06 (2H, m), 4.60 (2H, dd), 3.52 (2H, dd), 3.21 (1H, t), 2.94-2.76 (2H, m), 1.93-1.45 (4H, m). |
| [1.6] | [3-(4-Benzyl-4-hydroxy-piperidine-1-carbonyl)-5-(4-chloro-phenyl)-1-(2-chloro-phenyl)-1H-pyrazol-4-yl]-acetic acid | 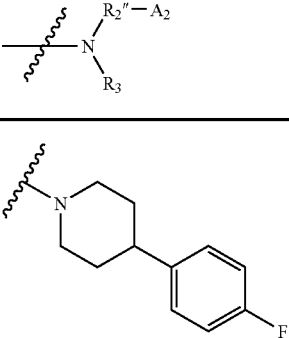 | —CH$_2$— | RT = 2.9 min. [M + 1]$^+$ = 563.2<br>δ (CDCl$_3$): 1.5-1.97 (4H, m), 2.82 (2H, s), 3.29 (1H, t), 3.52 (1H, t), 3.53-3.7 (2H, m), 4.63 (1H, d), 4.82 (1H, d), 7.06-7.57 (13H, m) |
| [1.7] | {1-(2-Chloro-phenyl)-5-(4-chloro-phenyl)-3-[4-(4-fluoro-phenyl)-4-hydroxy-piperidine-1-carbonyl]-1H-pyrazol-4-yl}-acetic acid | 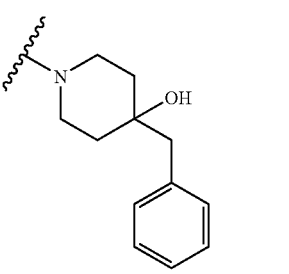 | —CH$_2$— | RT = 2.8 min. [M + H]$^+$ = 568 |
| [1.8] | [1-(2-Chloro-phenyl)-5-(4-chloro-phenyl)-3-(4'-hydroxy-3',4',5',6'-tetrahydro-2'H-[3,4']bipyridinyl-1'-carbonyl)-1H-pyrazol-4yl]-acetic acid | 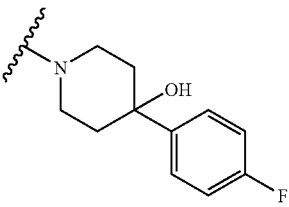 | —CH$_2$— | RT = 1.9 min. [M + H]$^+$ = 551 |
| [1.9] | [1-(2-Chloro-phenyl)-5-(4-chloro-phenyl)-3-(4'-hydroxy-3',4',5',6'-tetrahydro-2'H-[2,4']bipyridinyl-1'-carbonyl)-1H-pyrazol-4yl]-acetic acid | 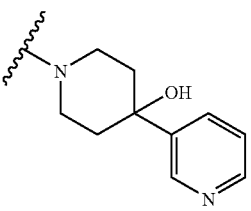 | —CH$_2$— | RT = 1.8 min. [M + H]$^+$ = 551 |
| [1.10] | {1-(2-Chloro-phenyl)-5-(4-chloro-phenyl)-3-[4-hydroxy-4-(4-trifluoromethyl-phenyl)-piperidine-1-carbonyl]-1H-pyrazol-4-yl}-acetic acid | 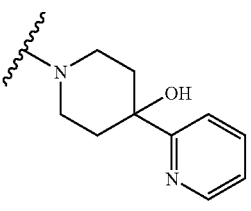 | —CH$_2$— | RT = 3.2 min. [M + H]$^+$ = 618.1 |

-continued

| Compound Number | Compound Name | 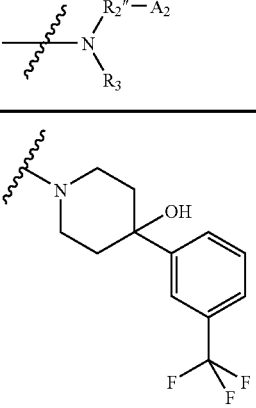 R₂″—A₂, R₃ | R₁ | Analysis LCMS/¹H NMR |
|---|---|---|---|---|
| [1.11] | {1-(2-Chloro-phenyl)-5-(4-chloro-phenyl)-3-[4-hydroxy-4-(3-trifluoromethyl-phenyl)-piperidine-1-carbonyl]-1H-pyrazol-4-yl}-acetic acid | 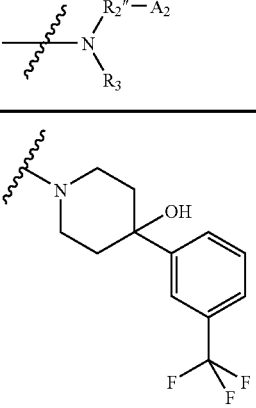 | —CH₂— | RT = 3.2 min. [M + H]⁺ = 618.0 |
| [1.12] | {1-(2-Chloro-phenyl)-5-(4-chloro-phenyl)-3-[4-(4-chloro-phenyl)-4-hydroxy-piperidine-1carbonyl]-1H-pyrazol-4-yl}-acetic acid | 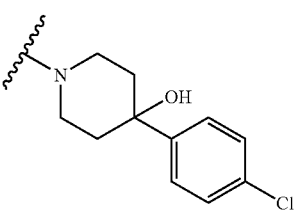 | —CH₂— | RT = 2.9 min. [M + H]⁺ = 586.1 |
| [1.13] | {1-(2-Chloro-phenyl)-5-(4-chloro-phenyl)-3-[4-(3-fluoro-phenyl)-piperidine-1-carbonyl]-1H-pyrazol-4-yl}-acetic acid | 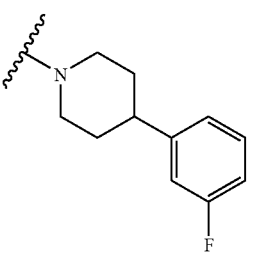 | —CH₂— | RT = 3.2 min. [M + H]⁺ = 552.1 |
| [1.14] | [1-(2-Chloro-phenyl)-5-(4-chloro-phenyl)-3-(4-hydroxy-4-phenyl-piperidine-1-carbonyl)-1H-pyrazol-4-yl]-acetic acid | 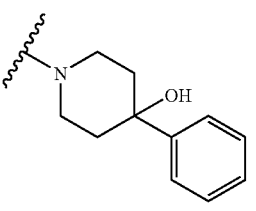 | —CH₂— | RT = 2.7 min. [M + H]⁺ = 550.1 |
| [1.15] | {1-(2-Chloro-phenyl)-5-(4-chloro-phenyl)-3-[3-(4-fluoro-phenyl)-pyrrol-idine-1-carbonyl]-1H-pyrazol-4-yl}-acetic acid | 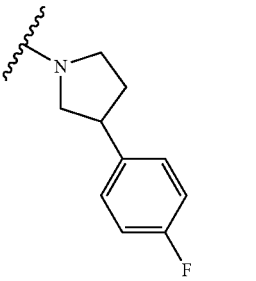 | —CH₂— | RT = 3.2 min. [M + H]⁺ = 538.1 |
| [1.16] | [5-(4-Chloro-phenyl)-1-(2-chloro-phenyl)-3-(4-pyrimidin-2-yl-piperazine-1-carbonyl)-1H-pyrazol-4-yl]-acetic acid | 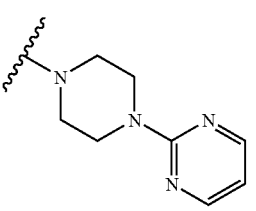 | —CH₂— | RT = 2.4 min. [M + 1]⁺ = 537.1 |

-continued

| Compound Number | Compound Name | R₂″—A₂ / N / R₃ | R₁ | Analysis LCMS/¹H NMR |
|---|---|---|---|---|
| [1.17] | {5-(4-Chloro-phenyl)-1-(2-chloro-phenyl)-3-[4-(4-fluoro-phenyl)-4-methoxy-piperidine-1carbonyl]-1H-pyrazol-4-yl}-acetic acid | 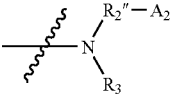 | —CH₂— | ¹H 300 MHz., DMSO: δ 7.53 (1H, d), 7.42-7.20 (8H, m), 7.15-7.04 (3H, m), 4.94 (1H, d), 4.74 (1H, d), 3.74-3.60 (2H, m), 3.52 (1H, d), 3.36 (1H, t), 3.04 (3H, s), 2.27-1.96 (4H, m). |
| [1.18] | [1-(2-Chloro-phenyl)-5-(4-chloro-phenyl)-3-(6-fluoro-3,4-dihydro-1H-isoquinoline-2-carbonyl)-1H-pyrazol-4-yl]-acetic acid | 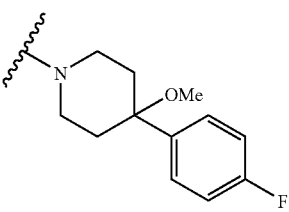 | —CH₂— | RT = 3.2 min. [M + H]⁺ = 524.1 |
| [1.19] | [1-(2-Chloro-phenyl)-5-(4-chloro-phenyl)-3-(6-trifluoromethyl-3,4-dihydro-1H-isoquinoline-2-carbonyl)-1H-pyrazol-4-yl]-acetic acid | 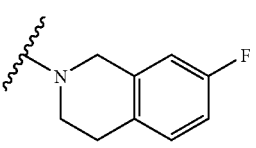 | —CH₂— | RT = 3.4 min. [M + H]⁺ = 574.1 |
| [1.20] | {1-(2-Chloro-phenyl)-5-(4-chloro-phenyl)-3-[4-(3-methyl-[1,2,4]oxadiazol-5-yl)-piperidine-1-carbonyl]-1H-pyrazol-4-yl}-acetic acid | 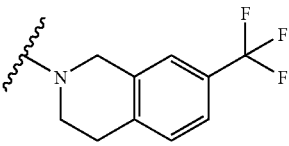 | —CH₂— | RT = 2.8 min. [M + H]⁺ = 540.1 |
| [1.21] | {1-(2-Chloro-phenyl)-5-(4-chloro-phenyl)-3-[4-(2-fluoro-phenyl)-4-hydroxy-piperidine-1carbonyl]-1H-pyrazol-4-yl}-acetic acid | 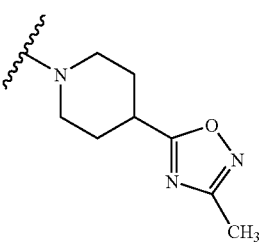 | —CH₂— | RT = 3.0 min. [M + H]⁺ = 568.1 |
| [1.22] | [5-(4-Chloro-phenyl)-1-(2-chloro-phenyl)-3-(4'-hydroxy-5-methyl-3',4',5',6'-tetrahydro-2'H-[2,4']bipyridinyl-1'-carbonyl)-1H-pyrazol-4-yl]-acetic acid | 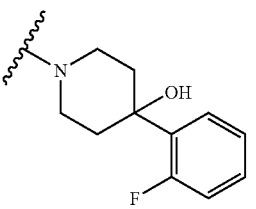 | —CH₂— | RT = 1.9 min. [M + H]⁺ = 565 |
| [1.23] | [5-(4-Chloro-phenyl)-1-(2-chloro-phenyl)-3-(4-thiophen-2-yl-piperidine-1-carbonyl)-1H-pyrazol-4-yl]-acetic acid | 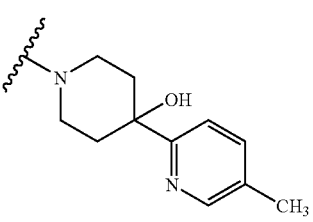 | —CH₂— | RT = 3.1 min. [M + H]⁺ = 540 |

-continued

| Compound Number | Compound Name | ![R2″-A2, N-R3 structure] | R₁ | Analysis LCMS/¹H NMR |
|---|---|---|---|---|
| [1.24] | [3-[4-(2-Bromo-thiazol-4-yl)-4-hydroxy-piperidine-1-carbonyl]-5-(4-chloro-phenyl)-1-(2-chloro-phenyl)-1H-pyrazol-4-yl]-acetic acid | 4-(2-bromothiazol-4-yl)-4-hydroxypiperidinyl | —CH₂— | RT = 2.7 min. [M + H]⁺ = 637 |
| [1.25] | {5-(4-Chloro-phenyl)-1-(2-chloro-phenyl)-3-[4-(2,3-difluoro-phenyl)-4-hydroxy-piperidine-1-carbonyl]-1H-pyrazol-4yl}-acetic acid | 4-(2,3-difluorophenyl)-4-hydroxypiperidinyl | —CH₂— | RT = 2.8 min. [M + H]⁺ = 586 |
| [1.26] | {1-(2-Chloro-phenyl)-5-(4-chloro-phenyl)-3-[4-(2,4-difluoro-phenyl)-piperidine-1-carbonyl]-1H-pyrazol-4-yl}-acetic acid | 4-(2,4-difluorophenyl)piperidinyl | —CH₂— | RT = 3.3 min. [M + H]⁺ = 570.1 |
| [1.27] | {1-(2-Chloro-phenyl)-5-(4-chloro-phenyl)-3-[4-(2-fluoro-phenyl)-piperidine-1-carbonyl]-1H-pyrazol-4-yl}-acetic acid | 4-(2-fluorophenyl)piperidinyl | —CH₂— | RT = 3.4 min. [M + H]⁺ = 552.1 |
| [1.28] | {1-(2-Chloro-phenyl)-5-(4-chloro-phenyl)-3-[4-(4-trifluoromethyl-phenyl)-piperidine-1-carbonyl]-1H-pyrazol-4-yl}-acetic acid | 4-(4-trifluoromethylphenyl)piperidinyl | —CH₂— | RT = 3.4 min. [M + H]⁺ = 602.0 |
| [1.29] | {1-(2-Chloro-phenyl)-5-(4-chloro-phenyl)-3-[4-(4-chloro-phenyl)-piperidine-1-carbonyl]-1H-pyrazol-4-yl}-acetic acid | 4-(4-chlorophenyl)piperidinyl | —CH₂— | RT = 3.4 min. [M + H]⁺ = 570.1 |

-continued

| Compound Number | Compound Name | $R_2'' - A_2$ structure with N-R_3 | $R_1$ | Analysis LCMS/$^1$H NMR |
|---|---|---|---|---|
| [1.30] | 3-{1-[4-Carboxymethyl-1-(2-chloro-phenyl)-5-(4-chloro-phenyl)-1H-pyrazole-3-carbonyl]-piperidin-4-yl}-benzoic acid | 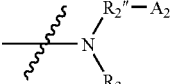 | —CH$_2$— | RT = 2.8 min. [M + H]$^+$ = 578.1 |
| [1.31] | {1-(2-Chloro-phenyl)-5-(4-chloro-phenyl)-3-[4-(3-chloro-phenyl)-piperidine-1-carbonyl]-1H-pyrazol-4-yl}-acetic acid | 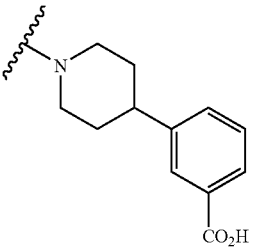 | —CH$_2$— | RT = 3.4 min. [M + H]$^+$ = 568.1 |
| [1.32] | [1-(2-Chloro-phenyl)-5-(4-chloro-phenyl)-3-(3,4,5,6-tetrahydro-2H-[4,4']bipyridinyl-1-carbonyl)-1H-pyrazol-4-yl]-acetic acid | 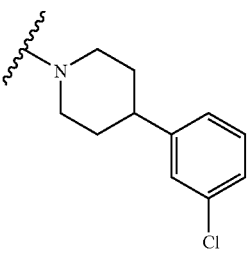 | —CH$_2$— | RT = 2.0 min. [M + H]$^+$ = 535.0 |
| [1.33] TM39882 | [1-(2-Chloro-phenyl)-5-(4-chloro-phenyl)-3-(4-phenyl-piperidine-1-carbonyl)-1H-pyrazol-4-yl]-acetic acid | 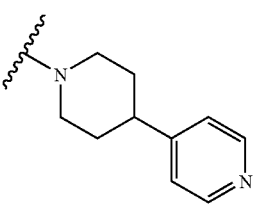 | —CH$_2$— | RT = 3.2 min. [M + H]$^+$ = 534.1 |
| [1.34] | {1-(2-Chloro-phenyl)-5-(4-chloro-phenyl)-3-[4-(3-cyano-phenyl)-piperidine-1-carbonyl]-1H-pyrazol-4-yl}-acetic acid | 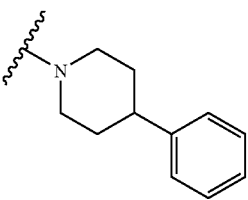 | —CH$_2$— | RT = 3.2 min. [M + H]$^+$ = 559.2 |
| [1.35] | {1-(2-Chloro-phenyl)-5-(4-chloro-phenyl)-3-[4-(3,5-dichloro-phenyl)-piperidine-1-carbonyl]-1H-pyrazol-4-yl}-acetic acid | 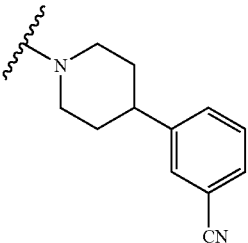 | —CH$_2$— | RT = 3.6 min. [M + H]$^+$ = 604.1 |

-continued

| Compound Number | Compound Name | R₂″—A₂ / N / R₃ | R₁ | Analysis LCMS/¹H NMR |
|---|---|---|---|---|
| [1.36] | {1-(2-Chloro-phenyl)-5-(4-chloro-phenyl)-3-[4-(3,5-difluoro-phenyl)-piperidine-1-carbonyl]-1H-pyrazol-4-yl}-acetic acid | 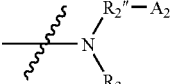 | —CH₂— | RT = 3.3 min. [M + H]⁺ = 570.1 |
| [1.37] | {1-(2-Chloro-phenyl)-5-(4-chloro-phenyl)-3-[4-(3-methoxy-phenyl)-piperidine-1-carbonyl]-1H-pyrazol-4-yl}-acetic acid | 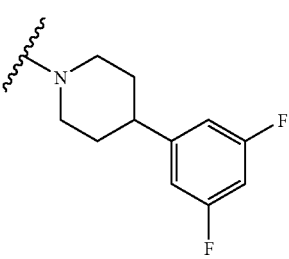 | —CH₂— | RT = 3.2 min. [M + H]⁺ = 564.1 |
| [1.38] | {1-(2-Chloro-phenyl)-5-(4-chloro-phenyl)-3-[2-(4-trifluoromethyl-phenyl)-pyrrolidine-1-carbonyl]-1H-pyrazol-4-yl}-acetic acid | 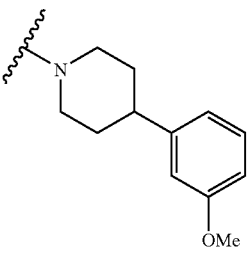 | —CH₂— | RT = 3.3 min. [M + H]⁺ = 588.1 |
| [1.39] | {1-(2-Chloro-phenyl)-5-(4-chloro-phenyl)-3-[3-(4-trifluoromethyl-phenyl)-pyrrolidine-1-carbonyl]-1H-pyrazol-4-yl}-acetic acid | 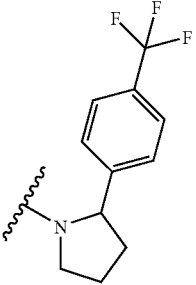 | —CH₂— | RT = 3.4 min. [M + H]⁺ = 588.1 |
| [1.40] | {1-(2-Chloro-phenyl)-5-(4-chloro-phenyl)-3-[4-(3-trifluoromethyl-phenyl)-piperidine-1-carbonyl]-1H-pyrazol-4-yl}-acetic acid | 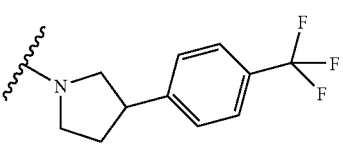 | —CH₂— | RT = 3.6 min. [M + H]⁺ = 602.1 |
| [1.41] | [1-(2-Chloro-phenyl)-5-(4-chloro-phenyl)-3-((S)-2-methoxymethyl-pyrrolidine-1-carbonyl]-1H-pyrazol-4-yl]-acetic acid | 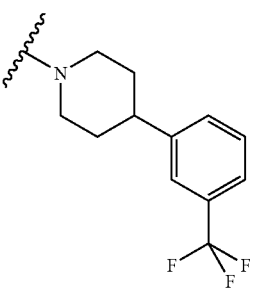 | —CH₂— | RT = 2.7 min. [M + H]⁺ = 488 |

| Compound Number | Compound Name | R₂″—A₂ / N—R₃ | R₁ | Analysis LCMS/¹H NMR |
|---|---|---|---|---|
| [1.42] | {1-(2-Chloro-phenyl)-5-(4-chloro-phenyl)-3-[4-(4-fluoro-3-trifluoromethyl-phenyl)-4-hydroxy-piperidine-1-carbonyl]-1H-pyrazol-4-yl}-acetic acid | 4-(4-fluoro-3-trifluoromethyl-phenyl)-4-hydroxy-piperidinyl | —CH$_2$— | RT = 3.0 min [M + H]$^+$ = 636 |
| [1.43] | [3-[4-(3-Chloro-4-fluoro-phenyl)-4-hydroxy-piperidine-1-carbonyl]-1-(2-chloro-phenyl)-5-(4-chloro-phenyl)-1H-pyrazol-4-yl]-acetic acid | 4-(3-chloro-4-fluoro-phenyl)-4-hydroxy-piperidinyl | —CH$_2$— | RT = 3.0 min [M + H]$^+$ = 602 |
| [1.44] | [1-(2-Chloro-phenyl)-5-(4-chloro-phenyl)-3-((3R,4R)-3-hydroxy-4-phenyl-piperidine-1-carbonyl)-1H-pyrazol-4-yl]-acetic acid | (3R,4R)-3-hydroxy-4-phenyl-piperidinyl | —CH$_2$— | RT = 2.9 min. [M + H]$^+$ = 550.1 |
| [1.45] | {1-(2-Chloro-phenyl)-5-(4-chloro-phenyl)-3-[4-(4-cyano-phenyl)-piperidine-1-carbonyl]-1H-pyrazol-4-yl}-acetic acid | 4-(4-cyano-phenyl)-piperidinyl | —CH$_2$— | RT = 3.2 min. [M + H]$^+$ = 559.1 |
| [1.46] | [1-(2-Chloro-phenyl)-5-(4-chloro-phenyl)-3-(pyrrolidine-1-carbonyl)-1H-pyrazol-4-yl]-acetic acid | pyrrolidinyl | —CH$_2$— | RT = 2.6 min [M + H]$^+$ = 444 |
| [1.47] | [1-(2-Chloro-phenyl)-5-(4-chloro-phenyl)-3-(piperidine-1-carbonyl)-1H-pyrazol-4-yl]-acetic acid | piperidinyl | —CH$_2$— | RT = 2.6 min [M + H]$^+$ = 458 |
| [1.48] | [1-(2-Chloro-phenyl)-5-(4-chloro-phenyl)-3-(morpholine-4-carbonyl)-1H-pyrazol-4-yl]-acetic acid | morpholinyl | —CH$_2$— | RT = 2.2 min [M + H]$^+$ = 460 |

| Compound Number | Compound Name | R₂″—A₂ / N / R₃ | R₁ | Analysis LCMS/¹H NMR |
|---|---|---|---|---|
| [1.49] | [3-(4-Benzyloxy-piperidine-1-carbonyl)-1-(2-chloro-phenyl)-5-(4-chloro-phenyl)-1H-pyrazol-4-yl]-acetic acid | 4-benzyloxy-piperidine | —CH₂— | RT = 3.0 min [M + H]⁺ = 564 |
| [1.50] | [1-(2-Chloro-phenyl)-5-(4-chloro-phenyl)-3-(4-hydroxymethyl-4-phenyl-piperidine-1-carbonyl)-1H-pyrazol-4-yl]-acetic acid | 4-hydroxymethyl-4-phenyl-piperidine | —CH₂— | RT = 2.8 min. [M + H]⁺ = 564.1 |
| [1.51] | {1-(2-Chloro-phenyl)-5-(4-chloro-phenyl)-3-[4-(2-cyano-phenyl)-piperidine-1-carbonyl]-1H-pyrazol-4-yl}-acetic acid | 4-(2-cyano-phenyl)-piperidine | —CH₂— | RT = 3.0 min. [M + H]⁺ = 559.1 δ (DMSO-D₆): 1.6-1.9 (4H, m), 2.9 (1H, t), 3.29 (2H, m), 3.6 (2H, m), 4.67 (2H, m), 7.24 (2H, d), 7.45-7.69 (9H, m), 7.8 (1H, d), 12.42 (1H, s). |
| [1.52] | 2-{1-(2-Chloro-phenyl)-5-(4-chloro-phenyl)-3-[4-(2-fluoro-phenyl)-piperidine-1-carbonyl]-1H-pyrazol-4-yl}-propionic acid | 4-(2-fluoro-phenyl)-piperidine | —CH(CH₃)— | RT = 3.2 min. [M + H]⁺ = 566.1 δ (DMSO-D₆): 1.35 (3H, t), 1.6-1.9 (4H, m), 2.88 (1H, q), 3.17 (2H, m), 3.61 (1H, quint), 4.28 (1H, t), 4.68 (1H, d), 7.16-7.56 (12H, m), 12.38 (1H, s). |
| [1.53] | {1-(2-Chloro-phenyl)-5-(4-chloro-phenyl)-3-[4-(2-methoxy-1-methyl-ethoxy-phenyl)-piperidine-1-carbonyl]-1H-pyrazol-4-yl}-acetic acid | 4-(2-methoxy-1-methyl-ethoxy-phenyl)-piperidine | —CH₂— | RT = 3.3 min. [M + H]⁺ = 576 |
| [1.54] | {1-(2-Chloro-phenyl)-5-(4-chloro-phenyl)-3-[4-(2-chloro-phenyl)-piperidine-1-carbonyl]-1H-pyrazol-4-yl}-acetic acid | 4-(2-chloro-phenyl)-piperidine | —CH₂— | RT = 3.3 min. [M + H]⁺ = 570.1 |

| Compound Number | Compound Name | $R_2''-A_2$ / $R_3$ group | $R_1$ | Analysis LCMS/$^1$H NMR |
|---|---|---|---|---|
| [1.55] | {1-(2-Chloro-phenyl)-5-(4-chloro-phenyl)-3-[3-(3-fluoro-phenyl)-pyrrolidine-1-carbonyl]-1H-pyrazol-4-yl}-acetic acid | 3-(3-fluorophenyl)pyrrolidin-1-yl | —CH$_2$— | RT = 3.4 min. [M + H]$^+$ = 538.0 |
| [1.56] | {1-(2-Chloro-phenyl)-5-(4-chloro-phenyl)-3-[trans-4-phenyl-3-methoxy-piperidine-1-carbonyl]-1H-pyrazol-4-yl}-acetic acid | trans-3-methoxy-4-phenylpiperidin-1-yl | —CH$_2$— | RT = 3.2 min. [M + H]$^+$ = 564.1 |
| [1.57] | {1-(2-Chloro-phenyl)-5-(4-chloro-phenyl)-3-[4-(3-methylsulfonyl-phenyl)-piperidine-1-carbonyl]-1H-pyrazol-4-yl}-acetic acid | 4-(3-methylsulfonylphenyl)piperidin-1-yl | —CH$_2$— | RT = 2.7 min. [M + H]$^+$ = 612 |
| [1.58] | {1-(2-Chloro-phenyl)-5-(4-chloro-phenyl)-3-[4-phenoxy)-piperidine-1-carbonyl]-1H-pyrazol-4-yl}-acetic acid | 4-phenoxypiperidin-1-yl | —CH$_2$— | RT = 3.2 min. [M + H]$^+$ = 550 |
| [1.59] | {1-(2-Chloro-phenyl)-5-(4-chloro-phenyl)-3-[4-(4-chlorophenoxy)-piperidine-1-carbonyl]-1H-pyrazol-4-yl}-acetic acid | 4-(4-chlorophenoxy)piperidin-1-yl | —CH$_2$— | UPLCMS: RT = 1.5 min. [M + H]$^+$ = 586.0 |
| [1.60] | {1-(2-Chloro-phenyl)-5-(4-chloro-phenyl)-3-[3-(4-fluorophenoxy)-azetidine-1-carbonyl]-1H-pyrazol-4-yl}-acetic acid | 3-(4-fluorophenoxy)azetidin-1-yl | —CH$_2$— | UPLCMS: RT = 1.4 min. [M + H]$^+$ = 540.1 |

| Compound Number | Compound Name | R₂″—A₂ / R₃ (N-substituent) | R₁ | Analysis LCMS/¹H NMR |
|---|---|---|---|---|
| [1.61] | {1-(2-Chloro-phenyl)-5-(4-chloro-phenyl)-3-[4-(3,4-difluorophenoxy)-piperidine-1-carbonyl]-1H-pyrazol-4-yl}-acetic acid | 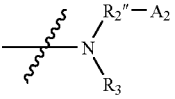 | —CH₂— | UPLCMS: RT = 1.4 min. [M + H]⁺ = 586.1 |
| [1.62] | {1-(2-Chloro-phenyl)-5-(4-chloro-phenyl)-3-[4-(3-fluorophenoxy)-piperidine-1-carbonyl]-1H-pyrazol-4-yl}-acetic acid | 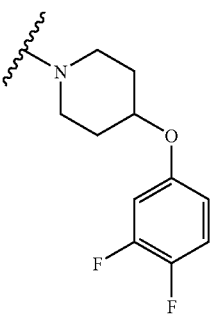 | —CH₂— | UPLCMS: RT = 1.4 min. [M + H]⁺ = 568.1 |
| [1.63] | {1-(2-Chloro-phenyl)-5-(4-chloro-phenyl)-3-[4-(5-fluoropyrimidin-2-oxy)-piperidine-1-carbonyl]-1H-pyrazol-4-yl}-acetic acid | 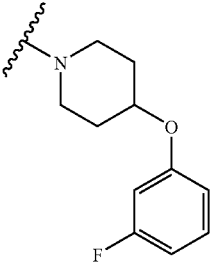 | —CH₂— | UPLCMS: RT = 1.2 min. [M + H]⁺ = 570.1 |
| [1.64] | {1-(2-Chloro-phenyl)-5-(4-chloro-phenyl)-3-[3-(4-fluorophenoxy)-pyrrolidine-1-carbonyl]-1H-pyrazol-4-yl}-acetic acid | 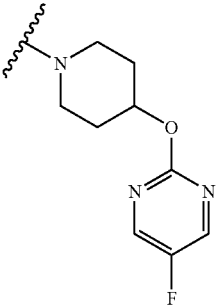 | —CH₂— | UPLCMS: RT = 1.4 min. [M + H]⁺ = 554.1 |
| [1.65] | {1-(2-Chloro-phenyl)-5-(4-chloro-phenyl)-3-[4-(2-fluoro-phenyl)-piperidine-1-carbonyl]-1H-pyrazol-4-yl}-2-hydroxy acetic acid | 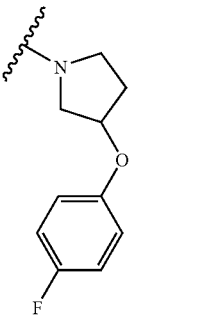 | —CH(OH)— | RT = 3.2 min. [M + H]⁺ = 568.4 |

Synthesis:

Compound [1.2]

Prepared according to the procedure outlined in the following scheme:

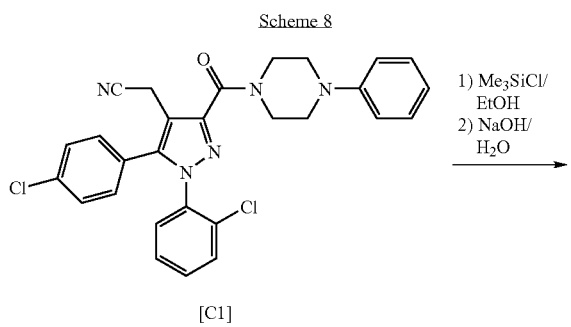

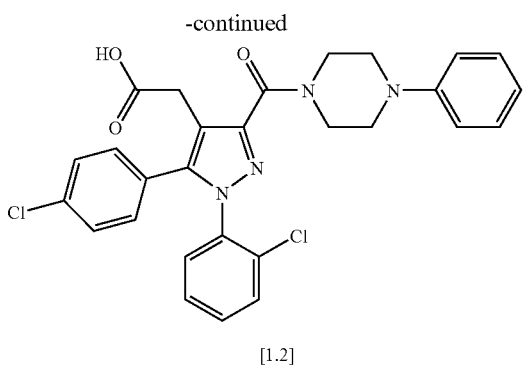

Chlorotrimethylsilane (0.36 ml, 2.8 mmol) was added to a stirred suspension of [C1] (0.10 g, 0.19 mmol) in ethanol (1.5 ml) under nitrogen at room temperature. The mixture was heated overnight at 60° C., cooled to room temperature and the solvent evaporated in vacuo. To the crude ester was added lithium hydroxide hydrate (23 mg, 0.6 mmol) in tetrahydrofuran/water (1:1, 6 ml) and stirred at room temperature for 16 hours then acidified by the addition of 1M hydrochloric acid and the precipitated compound filtered off and further purified by preparative HPLC to give the title compound [1.2] (10 mg).

Compound [1.1] was prepared by an analogous procedure to that described above from [C2] (N.B. dehydration occurred with [C2] during the first stage of this transformation.

Compound [1.3]

Prepared according to the procedure outlined in the following scheme:

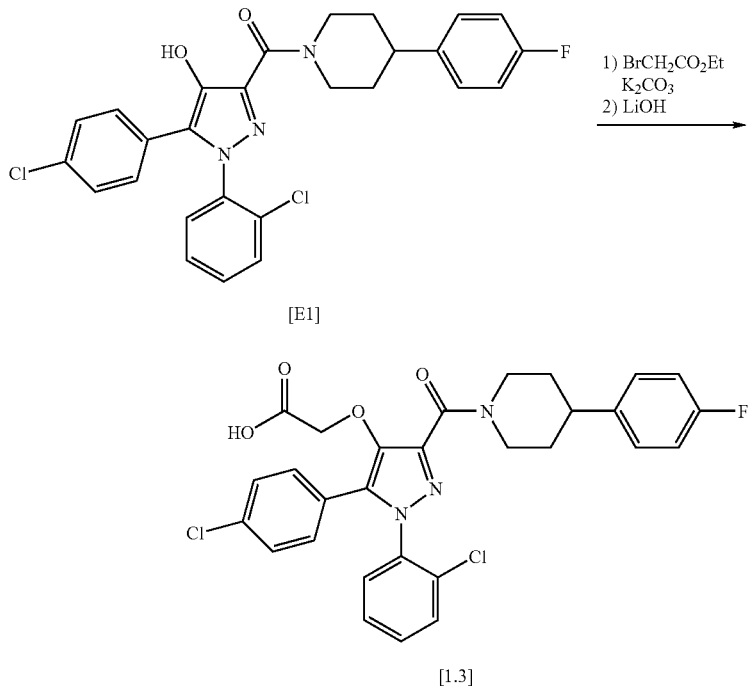

To a solution of [E1] (85 mg, 0.166 mmol) in acetone (0.5 ml) were added potassium carbonate (46 mg, 0.33 mmol) and ethyl 2-bromopropionate (20.3 ul, 0.183 mmol). The resulting suspension was stirred overnight at room temperature then partitioned between dichloromethane and brine. The organic phase was dried over anhydrous magnesium sulphate, filtered and evaporated in vacuo. The residue was purified by column chromatography over silica (2 g) silica, eluting with dichloromethane then ethyl acetate/heptane (1:1) to give {5-(4-Chloro-phenyl)-1-(2-chloro-phenyl)-3-[4-(4-fluoro-phenyl)-piperidine-1-carbonyl]-1H-pyrazol-4-yloxy}-acetic acid ethyl ester (77 mg, 78%) as a thick gum LCMS: RT=35 min. [M+H]$^+$=596.1

A mixture of this ester (77 mg, 0.129 mmol) and lithium hydroxide (22 mg, 0.51 mmol) in tetrahydrofuran/water (2 ml) was stirred overnight at room temperature. Tetrahydrofuran was evaporated in vacuo. The aqueous phase was acidified with 1 m hydrochloric acid, saturated with sodium chloride and extracted with dichloromethane. The organic phase was passed through a phase-separation filter and the solution evaporated in vacuo to give the crude which was purified by preparative chromatography to give [1.3] (46 mg, 0.087 mmol, 94%) as a white solid.

Compound [1.13]

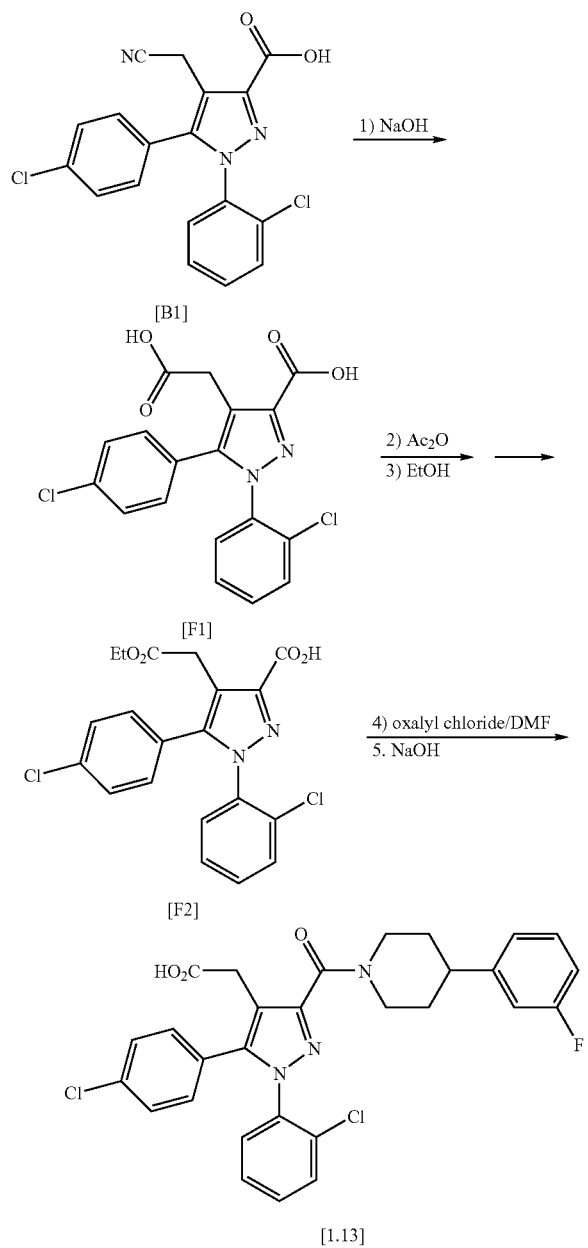

To nitrile (35 g) in ethanol (300 mL) was added sodium hydroxide (23 g) and the mixture heated to reflux overnight. After cooling the white disodium salt precipitate was filtered and washed twice with ethanol (50 mL) and dried overnight in a vacuum dessicator. The solid was then added to 500 mL water and acidified with 4N HCl, and the solid product was filtered off and dried for 72 h in a vacuum dessicator to give 36 g of diacid [F1]. To this product in toluene (300 mL) was added pyridine (2.2 mL) and acetic anhydride (15.6 mL) and the reaction stirred overnight at room temperature. Further amounts of pyridine (1 mL) and acetic anhydride (10 mL) were added and the reaction stirred 2 h at room temperature followed by 45 min at 50° C. Ethanol was then added (150 mL) and the reaction stirred 48 h at room temperature, concentrated in vacuo and the residue was purified by recrystallisation from ethanol to give monoester [F2] (15.6 g).

To monoester [F2] (0.3 g) in dichloromethane (2 mL) at ice bath temperature was added oxalyl chloride (0.13 mL) and DMF (1 drop) and the reaction stirred 30 min at this temp and 2 h at room temp. After concentration in vacuo, dichloromethane (2 mL) was added to the residue and the reaction cooled in an ice bath. DIPEA (0.46 mL) and 4-(3-fluorophenyl)-piperidine hydrochloride (0.17 g) was added and the reaction stirred overnight, concentrated and purified by chromatography to give the amide product (0.4 g). This product was hydrolysed using lithium hydroxide (0.1 g) in water (1.5 mL) and THF (2 mL), concentrated in vacuo and purified by recrystallisation from ethyl acetate and heptane to give [1.19] as a white solid (0.13 g)

Compounds [1.4]-[1.58] were prepared from [F2] using the relevant secondary amine an analogous fashion to that described for [1.13].

Compound [1.52]

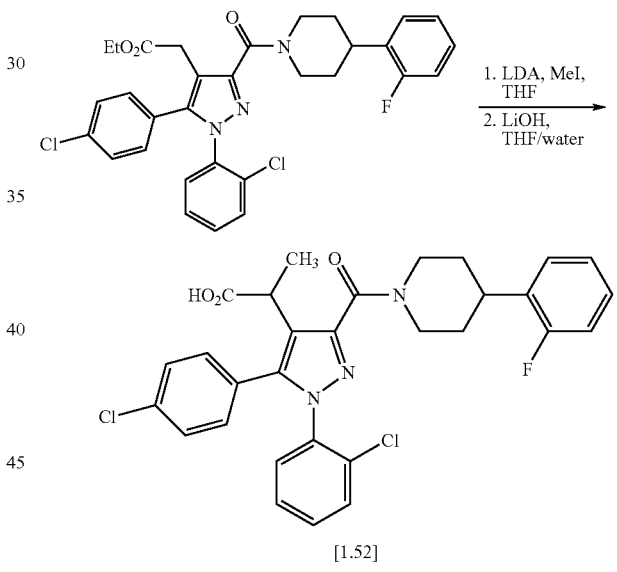

To a solution of LDA (0.86 mmol) −78° C. in 3 mL THF was added {1-(2-Chloro-phenyl)-5-(4-chloro-phenyl)-3-[4-(3-fluoro-phenyl)-piperidine-1-carbonyl]-1H-pyrazol-4-yl}-acetic acid ethyl ester (500 mg, 0.58 mmol), prepared as described for [1.13], step 4) in 1 mL THF, and the reaction stirred for 20 min at this temperature. Methyl iodide (0.27 mL, 4.3 mmol) in 5 ml THF was added and the reaction was allowed to warm up to −10° C. over 5 h, before addition of 0.5 mL ammonium chloride. The reaction was concentrated under reduced pressure and purified by preparative HPLC to give the ethyl ester (127 mg, LCMS RT=3.6 min. [M+H]$^+$= 594.1). Lithium hydroxide (100 mg) in a 1:1 mixture of THF water was added and the reaction mixture was stirred for 24 h, then partially concentrated under reduced pressure and purified by preparative chromatography to give the title compound Compound [1.65]

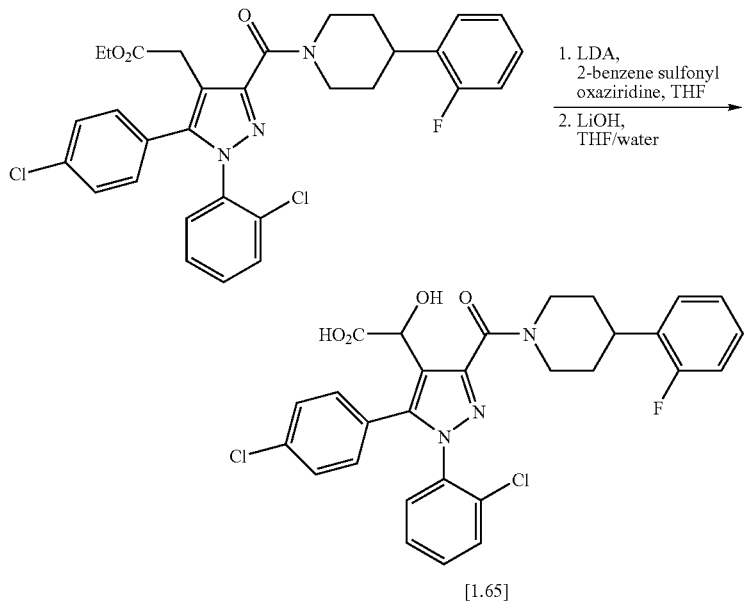

[1.65]

To a solution of LDA (0.46 mmol) −45° C. in 5 mL THF was added {1-(2-Chloro-phenyl)-5-(4-chloro-phenyl)-3-[4-(3-fluoro-phenyl)-piperidine-1-carbonyl]-1H-pyrazol-4-yl}-acetic acid ethyl ester (0.58 mmol, prepared as described for [1.13], step 4) in 1 mL THF, and the reaction stirred for 20 min at this temperature. 2-Benzene sulfonyl-3-oxaziridine (0.12 g, 0.46 mmol) in 1 ml THF was added and the reaction was allowed to warm up to −10° C. over 5 h, before addition of 0.5 mL ammonium chloride. The reaction was concentrated under reduced pressure, ethyl acetate (20 mL) was added, and the organic phase washed with water (4 mL) and concentrated to give the crude ester. (LCMS RT=3.6 min. [M+H]$^+$=596.1). Lithium hydroxide (100 mg) in a 1:1 mixture of THF water was added and the reaction mixture was stirred for 24 h, then partially concentrated under reduced pressure and purified by preparative chromatography to give the title compound Compounds of General Formula [2]

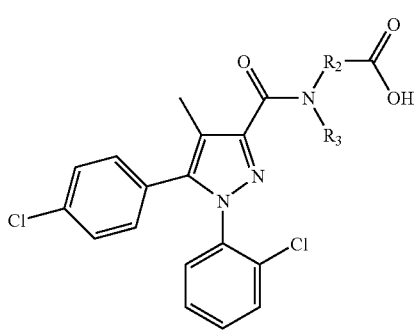

[2]

1-[5-(4-Chloro-phenyl)-1-(2-chloro-phenyl)-4-methyl-1H-pyrazole-3-carbonyl]-4-phenyl-piperidine-4-carboxylic acid [2.1]

Prepared according to the procedure outlined in the following scheme:

Scheme 9

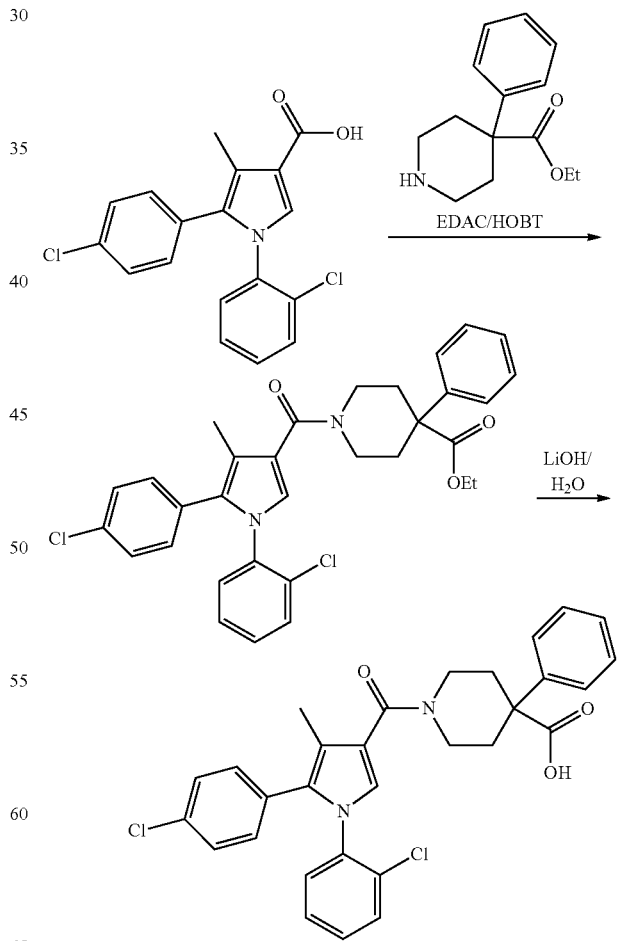

[2.1]

The ester compound [A1] was hydrolysed according to the procedure for the last step in the synthesis of [1.1]. The resulting acid was coupled with 4-phenyl-piperidine-4-carboxylic acid ethyl ester according to the procedure for the synthesis of [C1] to give 1-[1-(2-chloro-phenyl)-5-(4-chloro-phenyl)-4-methyl-1H-pyrazole-3-carbonyl]-4-phenyl-piperidine-4-carboxylic acid ethyl ester.

LCMS: RT=3.525 min. (M+H)⁺=548.1

A solution of lithium hydroxide hydrate (25 mg, 0.6 mmol) in water (0.5 ml) was added to a stirred solution of the product from the previous step (49 mg, 0.089 mmol) in tetrahydrofuran (0.5 ml). After 2 days, 3% hydrochloric acid was added to give a solution of pH2 that was extracted with dichloromethane (10 ml). The organic extracts were washed with brine, dried over anhydrous magnesium sulphate, filtered and evaporated in vacuo. The residue was purified by column chromatography over silica, eluting with ethyl acetate/heptane (9:1) to give the title compound [2.1] (14 mg, 0.026 mmol, 29%).

An analytically pure sample was obtained by preparative HPLC purification of this material under standard conditions.

LCMS: RT=2.940 min. (M+H)⁺=534.1

¹H NMR (DMSO-D₆): δ 2.10 (2H, t, br), 2.08 (3H, s), 2.44 (2H, d, br), 3.11 (1H, t, br), 3.37 (1H, t, br), 4.18 (1H, d, br), 4.38 (1H, d, br), 7.22 (2H, d), 7.27 (1H, d), 7.35 (2H, t), 7.40-7.47 (5H, m), 7.50 (1H, dd), 7.55-7.60 (2H, m).

Compounds of General Formula [3]

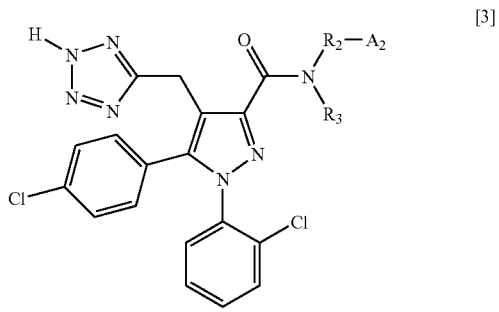

| Compound Number | Compound Name | | Analysis LCMS/¹H NMR |
|---|---|---|---|
| [3.1] | [5-(4-Chloro-phenyl)-1-(2-chloro-phenyl)-4-(2H-tetrazol-5-ylmethyl)-1H-pyrazol-3-yl]-(5-fluoro-1,3-dihydro-isoindol-2-yl)-methanone | | RT = 2.9 min, (M + H)⁺ = 534. δ (CDCl₃): 4.29 (2H, s), 5.10 (1H, s), 5.12 (1H, s), 5.37 (1H, s), 5.40 (1H, s), 7.00-7.45 (10H, m), 7.55 (1H, d), 15.12 (1H, s, br). |
| [3.2] | [1-(2-Chloro-phenyl)-5-(4-chloro-phenyl)-4-(2H-tetrazol-5-ylmethyl)-1H-pyrazol-3-yl]-[4-(4-fluoro-phenyl)-4-hydroxy-piperidin-1-yl]-methanone | | RT = 2.6 min [M + H]⁺ = 592 |
| [3.3] | [1-(2-Chloro-phenyl)-5-(4-chloro-phenyl)-4-(2H-tetrazol-5-ylmethyl)-1H-pyrazol-3-yl]-[4-(4-fluoro-phenyl)-piperidin-1-yl]-methanone | | RT = 3.1 min [M + H]⁺ = 576 ¹H NMR (300 MHz., DMSO): δ 7.64-7.56 (2H, m), 7.53-7.41 (4H, m), 7.34-7.25 (4H, m), 7.07-7.15 (2H, m), 4.6-4.4 (2H, m), 4.15 (2H, ABdd), 3.2-3.1 (1H, m), 2.85-2.65 (2H, m), 1.85-1.65 (2H, m), 1.55-1.48 (2H, m). |
| [3.4] | [1-(2-Chloro-phenyl)-5-(4-chloro-phenyl)-4-(2H-tetrazol-5-ylmethyl)-1H-pyrazol-3-yl]-[4-(2-fluoro-phenyl)-piperidin-1-yl]-methanone | | RT = 3.1 min. [M + 1]+ = 576 |

-continued

| Compound Number | Compound Name | 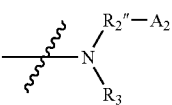 R₂″—A₂ structure | Analysis LCMS/¹H NMR |
|---|---|---|---|
| [3.5] | [1-(2-Chloro-phenyl)-5-(4-chloro-phenyl)-4-(2H-tetrazol-5-ylmethyl)-1H-pyrazol-3-yl]-[4-phenoxy-piperidin-1-yl]-methanone | 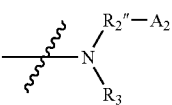 | UPLCMS: RT = 1.4 min. [M + 1]+ = 574.1 |
| [3.6] | [1-(2-Chloro-phenyl)-5-(4-chloro-phenyl)-4-(2H-tetrazol-5-ylmethyl)-1H-pyrazol-3-yl]-[4-(4-chlorophenoxy)-piperidin-1-yl]-methanone | 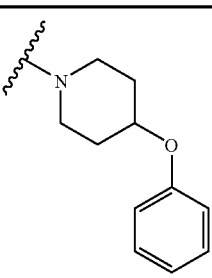 | UPLCMS: RT = 1.4 min. [M + 1]+ = 610.1 |
| [3.7] | [1-(2-Chloro-phenyl)-5-(4-chloro-phenyl)-4-(2H-tetrazol-5-ylmethyl)-1H-pyrazol-3-yl]-[3-(4-fluorophenoxy)-azetidin-1-yl]-methanone | 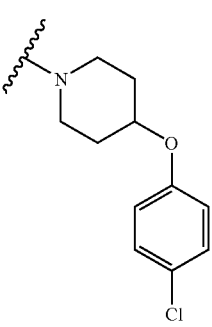 | UPLCMS: RT = 1.4 min. [M + 1]+ = 562.1 |
| [3.8] | [1-(2-Chloro-phenyl)-5-(4-chloro-phenyl)-4-(2H-tetrazol-5-ylmethyl)-1H-pyrazol-3-yl]-[4-(3,4-difluorophenoxy)-piperidin-1-yl]-methanone | 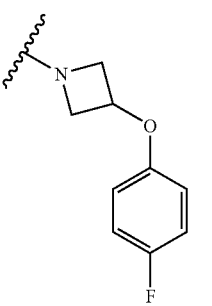 | UPLCMS: RT = 1.4 min. [M + 1]+ = 610.1 |
| [3.9] | [1-(2-Chloro-phenyl)-5-(4-chloro-phenyl)-4-(2H-tetrazol-5-ylmethyl)-1H-pyrazol-3-yl]-[4-(3-fluorophenoxy)-piperidin-1-yl]-methanone | 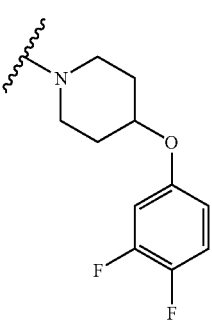 | UPLCMS: RT = 1.4 min. [M + 1]+ = 593.2 |

Synthesis:
Compound [3.1]
Prepared according to the procedure outlined in the following scheme:

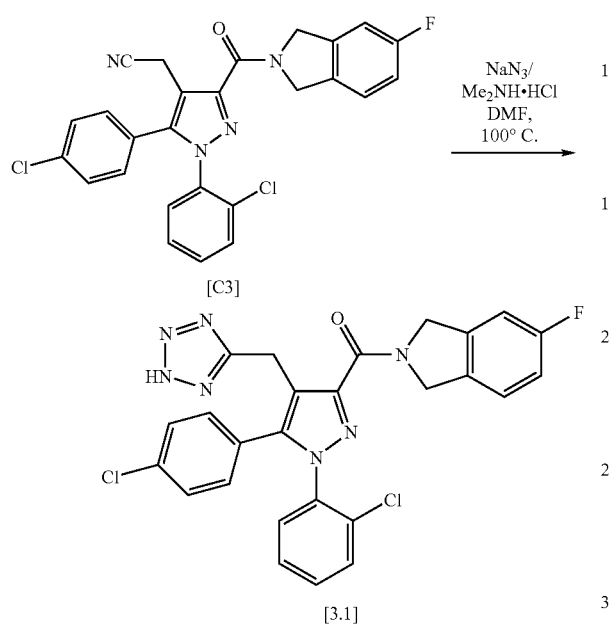

Sodium azide (28 mg, 0.24 mmol) and dimethylamonium hydrochloride (100 mg, 1.22 mmol) were added to a solution of [C3] (40 mg, 0.08 mmol) in N,N-dimethylformamide (1 ml) and the mixture heated at 120° C. for 12 hours. The mixture was cooled to room temperature and water (2 mL) followed by isopropanol/water to dissolution, acidified with 3% hydrochloric acid (10 ml) and extracted with ethyl acetate, dried and concentrated in vacuo. The crude product was purified by recrystallisation from ethyl acetate/heptane to give the title compound [3.1] (2.4 mg, 5.5%)

Compounds [3.2]-[3.4] were prepared from the intermediates [C2], [C4] and [C5] respectively, by an analogous procedure to that described for [3.1].

Intermediates of formula [C] were obtained from the respective intermediates of formula [B] and amines $R^3R^4NH$ by coupling either using 1-(3-dimethylaminopropyl)-3-ethylcarbodiimide hydrochloride (EDAC) and 1-hydroxybenzotriazole (HOBT) or by pre-formation of the acid chloride with oxalyl chloride and catalytic N,N-dimethylformamide Compounds of General Formula [4]

Prepared via intermediate [A2] using the same procedure as outlined in Scheme (6) and Scheme (10) and described for compound [3.1] (for [4.1] and [4.3]), and correspondingly as described for [1.13] (for [4.2] and [4.4]).

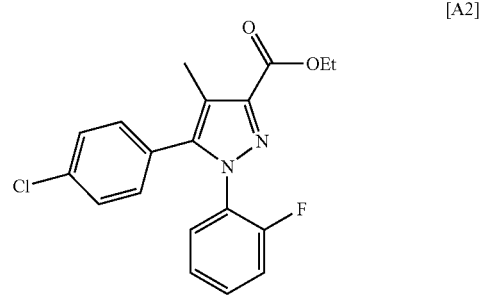

[A2] was prepared in a similar manner to intermediate [A1] but where 2-chlorophenylhydrazine was replaced by 2-flourophenylhydrazine

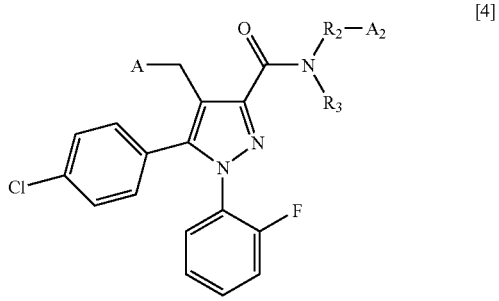

| Compound Number | Compound Name | A | $R_2''-A_2$ / N \ $R_3$ | Analysis UPLCMS |
|---|---|---|---|---|
| [4.1] | [1-(2-Fluoro-phenyl)-5-(4-chloro-phenyl)-4-(2H-tetrazol-5-ylmethyl)-1H-pyrazol-3-yl]-[4-(4-chlorophenoxy)-piperidin-1-yl]-methanone | 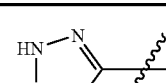 | 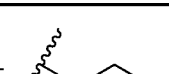 | RT = 1.4 min. [M + 1]+ = 593.2 |

-continued

| Compound Number | Compound Name | A ⟶ | $R_2''-A_2$ / N \ $R_3$ | Analysis UPLCMS |
|---|---|---|---|---|
| [4.2] | [1-(2-Fluoro-phenyl)-5-(4-chloro-phenyl)-4-(2H-tetrazol-5-ylmethyl)-1H-pyrazol-3-yl]-[4-(2-fluoro-phenyl)-piperidin-1-yl]-methanone | tetrazolylmethyl group | 4-(2-fluorophenyl)piperidinyl | RT = 1.3 min. [M + 1]+ = 560.1 |
| [4.3] | 2-{1-(2-Fluoro-phenyl)-5-(4-chloro-phenyl)-3-[4-(4-chlorophenoxy)-piperidine-1-carbonyl]-1H-pyrazol-4-yl}-propionic acid | propionic acid group | 4-(4-chlorophenoxy)piperidinyl | RT = 1.4 min. [M + 1]+ = 568.1 |
| [4.4] | {1-(2-Fluoro-phenyl)-5-(4-chloro-phenyl)-3-[4-(2-fluoro-phenyl)-piperidine-1-carbonyl]-1H-pyrazol-4-yl}-acetic acid | acetic acid group | 4-(2-fluorophenyl)piperidinyl | RT = 1.4 min. [M + 1]+ = 536.1 |

Biological Data:

Compounds were tested in the functional Cannabinoid Receptor-1 assay described below, and their $IC_{50}$ values for antagonizing a CB1 receptor agonist were assessed.

Compounds [1.1], [1.3], [1.4], [1.5], [1.6], [1.7], [1.10], [1.11], [1.12], [1.13], [1.14], [1.15], [1.17], [1.19], [1.21], [1.23], [1.24], [1.25], [1.26], [1.27], [1.28], [1.29], [1.31], [1.33], [1.34], [1.35], [1.36], [1.37], [1.38], [1.39], [1.40], [1.42], [1.43], [1.45], [1.49], [1.50], [1.51], [1.52], [1.53], [1.54], [1.55], [1.56], [1.58], [1.59], [1.60], [1.61], [1.62], [1.63], [1.64], [1.65], [2.1], [3.2], [3.3], [3.4]], [3.5], [3.6], [3.7], [3.8], [3.9] [4.1], [4.2], [4.3], [4.4], had $IC_{50}$ value lower than 0.30 µM.

Compounds [1.2], [1.9], [1.16], [1.18], [1.20], [1.22], [1.32], [1.41], [1.44], [1.46], [1.47], [3.1], [1.57], had $IC_{50}$ value between 0.3 µM and 3.0 µM Compound [1.8], [1.30], [1.48], had $IC_{50}$ value between 3.0 µM and 10 µM Biological Evaluation Transfection and Cell Culture—The cDNA encoding the human CB1 (Cannabinoid Receptor-1) receptor (GenBank accession number NM_016083) was cloned from a human adipose tissue cDNA library and cloned into the eukaryotic expression vector pcDNA3.1 (Invitrogen).

Chinese Hamster Ovary cells (CHO-K1) stably expressing recombinant human CB1 were generated by transfecting the plasmid containing the coding sequence of the human CB1 receptor in CHO-K1 cells, using lipofectamin, according to the manufacturer instructions. Resistant clones were selected in the presence of 600 µg/ml G418 (Life technology). Stably transfected CHO-K1 cells were maintained in Ham's F-12 culture medium (Invitrogen), supplemented with 10% fetal calf serum (Invitrogen), 100 U/ml penicillin, 100 µg/ml streptomycin (Life Technology), and 600 µg/ml G418.

Cannabinoid Receptor-1 Functional Assay.

Functional activities of the above examples of compounds of the invention were assessed in vitro by measuring their ability to inhibit CP55940-induced [$^{35}$S]GTPγS binding to membranes prepared from CHO-K1 cells expressing the human CB1 receptor (described in Transfection and Cell Culture). CP55940 is a well known non-selective CB1 and CB2 receptor agonist (e.g Felder et al., 1995, Molecular Pharmacology, (48) 443-50). Membranes were prepared by a standard procedure. Briefly, cells were harvested using 10 mM EDTA and collected by centrifugation. Pelleted cells were homogenized in ice-cold 20 mM Hepes (pH 7.4), 10 mM EDTA and protease inhibitors (Complete protease inhibitor cocktail tablet, Roche) using an Ultra Turrax Homogenizer. The homogenate was centrifuged at 14 000 rpm for 45 min. at 4° C. The resultant pellet was resuspended in the same buffer but with only 0.1 mM EDTA and was again centrifuged at 14 000 rpm for 45 min. at 4° C. The resulting pellet (membranes) was resuspended in 20 mM Hepes (pH 7.4), 0.1 mM EDTA, 2 mM $MgCl_2$ and protease inhibitors and protein concentration was determined by Micro BCA Protein Assay Reagent Kit (Pierce Biotechnology) according to the manufacturer instructions. The [$^{35}$S]GTPγS SPA (Scintillation Proximity Assay) binding assay was performed by incubating 5 µg/well hCB1-membranes with 1 nM [$^{35}$S]GTPγS (Perkin Elmer—NEG 030H) in the presence of 3 nM of CP55940 and various concentrations of the test compounds at room temperature for 1 hr in 96-well microtiter plates. 0.4 mg/well SPA beads (PVT-WGA; RPNQ0001 Amersham Pharmacia Biotech) were then added and the incubation continued for further 30 min. on an orbital shaker. The assay buffer contained 50 mM HEPES (pH 7.5), 50 mM NaCl, 2.5 mM $MgCl_2$, 0.1% BSA, 1 μM GDP and 100 μg/ml Saponin. Microtiter plates were centrifuged at 1500 rpm for 5 min. and radioactivity was read immediately using a Topcounter (PerkinElmer Life Sciences). Data were analyzed and IC50 values determined by non-linear regression using the Prism software (GraphPad Software, San Diego).

In Vivo Model Measuring Effect on Gastrointestinal Transit

Test compounds were evaluated for in vivo efficacy by testing for antagonism of the effects of the CB1 (cannabinoid receptor 1) agonist R-(+)-WIN 55,212, on gastrointestinal transit in male NMRI mice (weighing 20-30 g at entrance, with 5 g as maximum range per experiment). The method follows that described by Lacroix and Guillaume (*Current Protocols in Pharmacology*, Wiley, N.Y., 5.3.1.-5.3.8., 1998).

The CB1 receptor has been implicated in the control of the gastrointestinal transit in rodents. Stimulation with a CB1 agonist, such as R-(+)-WIN 55,212, decreases the transit time of the gastrointestinal tract which can be blocked by a CB1 antagonist (eg rimonabant). The transit time after R-(+)-WIN 55,212 treatment is unchanged in mice with a genetic deletion of the CB1 receptor. It has also been shown that administration of a CB1 antagonist alone can exert the opposite effect of a CB1 agonist; to increase the transit time (eg Izzo et al., European Journal of Pharmacology, 384 (1999):37-42 and Carai et al., British Journal of Pharmacology (2006): 1-8). Scientific literature suggests that the action of CB1 agonists and antagonists primarily are mediated via peripheral CB1 receptors in the gut (eg Casu et al., European Journal of Pharmacology, 459 (2003):97-105).

The model described has been widely used for the in vivo characterization of CB1 antagonists. Rimonabant, which is clinically active for the treatment of obesity, has shown a clear dose dependent effect in the model further supporting the relevance of this model for measuring CB1 receptor in vivo efficacy.

Animals are maintained on a normal phase 12 hour light-dark cycle. Food (standard chow) and water are provided ad libitum, unless otherwise stated. Test compounds are dissolved in vehicle 1: 5% NMethylpyrrolidone (Sigma) and 10% Solutol (HS-15 from BASF) in water and dosed orally by gavage (p.o.) with an administration volume of 5 ml/kg. R-(+)-WIN 55,212 (Sigma) is dispersed in 1% DMSO and 49.5% 2-hydroxypropyl-beta-cyclodextrin in distilled water (vehicle 2) and dosed intraperitoneal (i.p.) with an administration volume of 10 ml/kg. 7 mice are used for each treatment group.

The gastrointestinal transit experiment is initiated after overnight food deprivation of the mice. The mice are administered a suspension of 10% charcoal (0.4 ml/mouse orally by gavage). 2.5% Gum arabic is used as solvent for charcoal. The animals are sacrificed 20 minutes later by cervical dislocation and the small intestine is removed from the cardia to the caecum. The distance covered by the head of the marker is measured and expressed as percent of the total length of the small intestine.

The effect of test compounds are evaluated at one or more doses, administered p.o. 45 minutes before R-(+)-WIN 55,212 (2.5 mg/kg) which is administered i.p. 30 minutes before charcoal.

FIG. 1 shows the effect on gastrointestinal transit after i.p. administration of the CB1 agonist R-(+)-WIN 55,212 (2.5 mg/kg) with or without the pre-treatment (45 min.) of Example 1.34 (10 mg/kg p.o.) or rimonabant (3 mg/kg p.o.).

The invention claimed is:

1. A compound of formula (IB), or a salt, single enantiomer or N-oxide thereof:

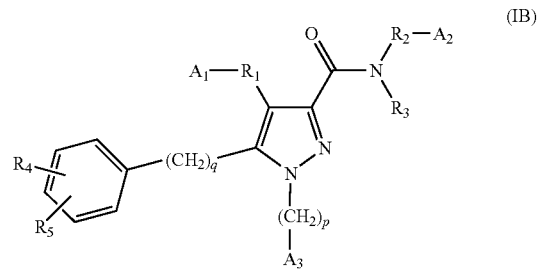

WHEREIN:
$A_1$ is tetrazolyl;
p and q are independently 0 or 1;
$A_3$ is phenyl or cycloalkyl, either of which is optionally substituted with $R_4$ and/or $R_5$;
$R_4$ and $R_5$ independently —$R_9$, —CN, —F, —Cl, —Br, —$OR_9$, —$NR_7R_8$, —$NR_7COR_6$, —$NR_7SO_2R_6$, —$COR_6$, —$SR_9$, —$SOR_9$ or —$SO_2R_6$;
$R_6$ is $C_1$-$C_4$ alkyl, cycloalkyl, —$CF_3$ or —$NR_7R_8$;
$R_7$ and $R_8$ are independently hydrogen, $C_1$-$C_4$ alkyl or cycloalkyl;
$R_9$ is hydrogen, $C_1$-$C_4$ alkyl, $C_1$-$C_4$ alkoxy, $C_1$-$C_4$ alkoxy ($C_1$-$C_4$ alkyl)-, cycloalkyl, fully or partially fluorinated $C_1$-$C_4$ alkyl;
$R_1$ is (i) a bond, or
(ii) —$(CH_2)_a B_1 (CH_2)_b$— wherein a and b are independently 0, 1, 2 or 3 provided that a+b is not greater than 4, and $B_1$ is —CO—, —O—, —S—, —SO—, —$SO_2$—, —$CH_2$—, —CHOH— or —$NR_7$—; or
(iii) a divalent radical selected from —C($R_{10}$)($R_{11}$)—*, —C($R_{10}$)($R_{11}$)—O—*, —C($R_{10}$)($R_{11}$)$CH_2$—*, —C($R_{10}$)($R_{11}$)$CH_2$—O—*, —$CH_2$C($R_{10}$)($R_{11}$)—*, —$CH_2$C($R_{10}$)($R_{11}$)—O—*, —$CH_2$—O—C($R_{10}$)($R_{11}$)—* and —C($R_{10}$)($R_{11}$)—O—$CH_2$—*, wherein the bond indicated by an asterisk is attached to the pyrazole ring;
$R_{10}$ is hydrogen and $R_{11}$ is ($C_1$-$C_3$)alkyl; or $R_{10}$ and $R_{11}$ are both ($C_1$-$C_3$)alkyl; or $R_{10}$ and $R_{11}$ taken together with the carbon atom to which they are attached form a ($C_3$-$C_5$)cycloalkyl ring; and
the group —N($R_3$)$R_2$-$A_2$ has formula (II) or (IV):

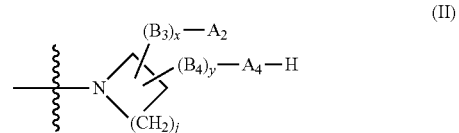

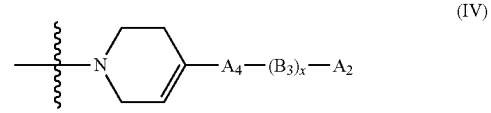

wherein x and y are independently 0 or 1, and j is 1, 2, 3 or 4;

$B_3$ is —$C(R_{13})(R_{14})$—, —O—, or —$NR_7$—, or in either orientation —O—$C(R_{13})(R_{14})$—, —$CH_2$—$C(R_{13})(R_{14})$—;

$B_4$ is —$C(R_{13})(R_{14})$—, —CO—, —$SO_2$—, —O—, or in either orientation O—$C(R_{13})(R_{14})$—, —$CH_2$—$C(R_{13})(R_{14})$—;

$A_2$ is hydrogen, —COOH, tetrazolyl, —CN, —$CF_3$, —$COR_6$, —$SO_2R_6$, —$OR_9$, —$NR_7R_8$, —$NR_7COR_6$, or —$NR_7SO_2R_6$;

$A_4$ is a monocyclic carbocyclic or monocyclic heterocyclic ring, having 3 to 8 ring atoms, optionally substituted with one or more of —F, —Cl, —Br, —CN, —$CF_3$, $C_1$-$C_4$ alkyl, cycloalkyl, —$OR_9$, oxo or —$NR_7R_8$; and $R_{13}$ and $R_{14}$ are independently hydrogen or $(C_1$-$C_3)$alkyl; or $R_{13}$ and $R_{14}$ are both $(C_1$-$C_3)$alkyl; or $R_{13}$ and $R_{14}$ taken together with the carbon atom to which they are attached form a $(C_3$-$C_5)$cycloalkyl ring.

2. A compound as claimed in claim 1 wherein:

$R_9$ is hydrogen, $C_1$-$C_4$ alkyl, cycloalkyl, fully or partially fluorinated $C_1$-$C_4$ alkyl; and $B_4$ is —$C(R_{13})(R_{14})$—, —CO—, —$SO_2$—, or —O—CH.

3. A compound of formula (I), or a salt, single enantiomer or N-oxide thereof:

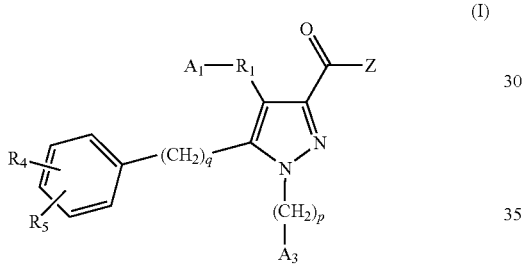

(I)

WHEREIN:
$A_1$ is tetrazolyl;
p and q are independently 0 or 1;
$A_3$ is phenyl or cycloalkyl, either of which is optionally substituted with $R_4$ and/or $R_5$;
$R_4$ and $R_5$ are independently —$R_9$, —CN, —F, —Cl, —Br, —$OR_9$, —$NR_7R_8$, —$NR_7COR_6$, —$NR_7SO_2R_6$, —$COR_6$, —$SR_9$, —$SOR_9$, or —$SO_2R_6$;
$R_6$ is $C_1$-$C_4$ alkyl, cycloalkyl, —$CF_3$ or —$NR_7R_8$;
$R_7$ and $R_8$ are independently hydrogen, $C_1$-$C_4$ alkyl or cycloalkyl;
$R_9$ is hydrogen, $C_1$-$C_4$ alkyl, $C_1$-$C_4$ alkoxy, $C_1$-$C_4$ alkoxy$(C_1$-$C_4$ alkyl)-, cycloalkyl, or fully or partially fluorinated $C_1$-$C_4$ alkyl;
$R_1$ is (i) a bond;
(ii) a divalent radical of formula —$(CH_2)_aB_1(CH_2)_b$— wherein a and b are independently 0, 1, 2 or 3 provided that a+b is 1, 2 or 3, and $B_1$ is —CO—, —O—, —S—, —SO—, —$SO_2$—, —$CH_2$—, —$CHCH_3$—, —CHOH— or —$NR_7$—; or
(iii) a divalent radical selected from —$C(R_{10})(R_{11})$—*, —$C(R_{10})(R_{11})$—O—*, —$C(R_{10})(R_{11})CH_2$—*, —$C(R_{10})(R_{11})CH_2$—O—*, —$CH_2C(R_{10})(R_{11})$—*, —$CH_2C(R_{10})(R_{11})$—O—*, —$CH_2$—O—$C(R_{10})(R_{11})$—* and —$C(R_{10})(R_{11})$—O—$CH_2$—*, wherein the bond indicated by an asterisk is attached to the pyrazole ring;

Z is selected from morpholin-1-yl and radicals of formula (II)

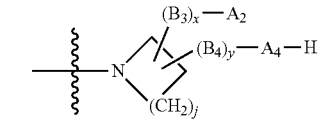

(II)

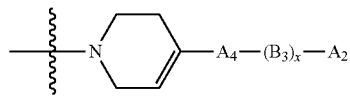

(IV)

wherein
x and y are independently 0 or 1,
j is 1, 2, 3 or 4,
$A_2$ is hydrogen, —COOH, tetrazolyl, —CN, —$CF_3$, —$COR_6$, —$SO_2R_6$, —$OR_9$, —$NR_7R_8$, —$NR_7COR_6$, or —$NR_7SO_2R_6$,
$A_4$ is a bond or
(i) a monocyclic carbocyclic ring, having 3 to 8 ring atoms, optionally substituted with one or more of —F, —Cl, —Br, —CN, —$CF_3$, $C_1$-$C_4$ alkyl, cycloalkyl, —$OR_9$, oxo or —$NR_7R_8$ or $SO_2R_6$; or
(ii) a monocyclic heterocyclic ring, having 4 to 8 ring atoms, optionally substituted with one or more of —F, —Cl, —Br, —CN, —$CF_3$, $C_1$-$C_4$ alkyl, cycloalkyl, —$OR_9$, oxo or —$NR_7R_8$ or $SO_2R_6$,
provided that for formula (IV), when $A_4$ is a bond, $B_3$ is not attached to $A_4$ by an oxygen or nitrogen
$B_3$ is —$C(R_{13})(R_{14})$—, —O—, or —$NR_7$—, or in either orientation —O—$C(R_{13})(R_{14})$—, or —$CH_2$—$C(R_{13})(R_{14})$— provided that for formulae (II)-(V), when x is 1 and $B_3$ is attached to $A_2$ by oxygen or nitrogen, then $A_2$ is hydrogen;
$B_4$ is —$C(R_{13})(R_{14})$—, —CO—, —$SO_2$—, —O—, or in either orientation —O—$C(R_{13})(R_{14})$—, or —$CH_2$—$C(R_{13})(R_{14})$—;
$R_{10}$ is hydrogen and $R_{11}$ is $(C_1$-$C_3)$alkyl or —OH; or $R_{10}$ and $R_{11}$ are both $(C_1$-$C_3)$alkyl; or $R_{10}$ and $R_{11}$ taken together with the carbon atom to which they are attached form a $(C_3$-$C_5)$cycloalkyl ring; and
$R_{13}$ and $R_{14}$ are independently hydrogen or $(C_1$-$C_3)$alkyl; or $R_{13}$ and $R_{14}$ are both $(C_1$-$C_3)$alkyl; or $R_{13}$ and $R_{14}$ taken together with the carbon atom to which they are attached form a $(C_3$-$C_5)$cycloalkyl ring.

4. A compound as claimed in claim 3 wherein the radical $R_1$ is —$CH_2$—, —$CH_2O$—*, or —$CH_2OCH_2$—.

5. A compound as claimed in claim 3 wherein $R_4$ is hydrogen and $R_5$ is other than hydrogen and is in the position para to —$(CH_2)_q$—.

6. A compound as claimed in claim 3 wherein, $R_4$ is hydrogen and $R_5$ is other than hydrogen and is in the position ortho to —$(CH_2)_p$—.

7. A compound as claimed in claim 3 wherein Z has formula:

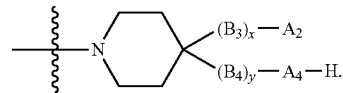

8. A compound as claimed in claim 3 wherein $B_3$ is present and is —$C(R_{13})(R_{14})$—, or in either orientation —O—$C(R_{13})(R_{14})$—, —$CH_2$—$C(R_{13})(R_{14})$—, or —NR$_7$—, wherein R$_{13}$ and R$_{14}$ are independently hydrogen or methyl; and R$_7$ is hydrogen, methyl or cyclopropyl.

9. A compound as claimed in claim 3 wherein B$_4$ is present and is —C(R$_{13}$)(R$_{14}$)—, wherein R$_{13}$ and R$_{14}$ are independently hydrogen or methyl.

10. A compound as claimed in claim 3 wherein A$_4$ is present and is selected from the group consisting of phenyl, pyridine, pyrimidine, thiophene, furan, oxazole and thiazole rings.

11. A compound as claimed in claim 3 wherein when A$_2$ is —SO$_2$R$_6$, —OR$_9$, —NR$_7$R$_8$, —NR$_7$COR$_6$, or —NR$_7$SO$_2$R$_6$ then R$_6$ is selected from methyl or —CF$_3$; and R$_7$, R$_8$ and R$_9$ are independently selected from hydrogen or methyl.

12. A compound as claimed in claim 3 wherein, in Z, x and y are both 0 and A$_2$ is hydrogen, methyl, —CN, —OH, or —COOH.

13. A compound as claimed in claim 3 wherein the radical —C(═O)Z is selected from the group consisting of radicals of formulae (C)-(P):

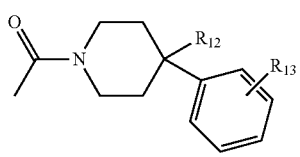
(C)

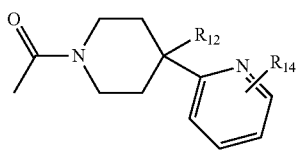
(D)

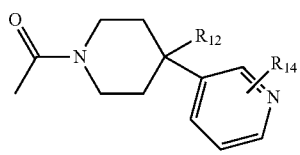
(E)

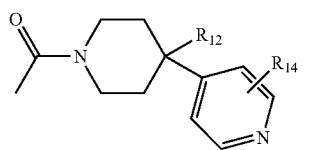
(F)

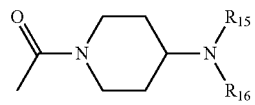
(G)

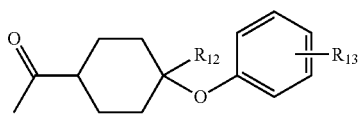
(K)

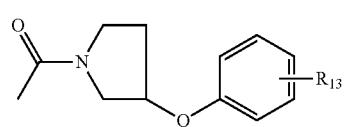
(L)

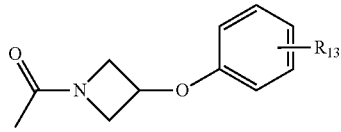
(M)

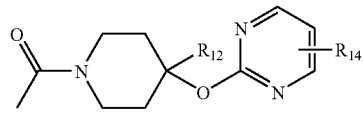
(N)

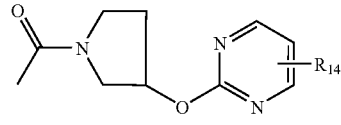
(O)

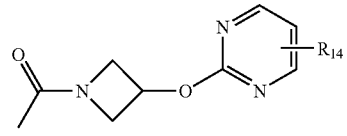
(P)

wherein

R$_{12}$ is selected from hydrogen, —CH$_3$, —OH, —CN and —COOH;

R$_{13}$ is selected from hydrogen, —F, —CF$_3$, —OCF$_3$, —Br.—Cl, —OCH$_3$, —CH$_3$, —CN and —COOH;

R$_{14}$ is selected from hydrogen, —F, —CF$_3$, —OCF$_3$, —Br.—Cl, —OCH$_3$, —CH$_3$, —CN, —OH, and —COOH;

R$_{15}$ and R$_{16}$ are independently selected from hydrogen and (C$_1$-C$_6$)alkyl or R$_{15}$ and R$_{16}$ taken together with the nitrogen to which they are attached form a cyclic amino ring of 4 to 7 ring atoms;

R$_{17}$ is selected from hydrogen, (C$_1$-C$_6$)alkyl, (C$_1$-C$_6$)alkylC(═O)—, (C$_1$-C$_6$)alkylSO$_2$—, benzyloxycarbonyl-, and —C(═O)OCH$_3$.

14. A compound as claimed in claim 13 wherein radical —C(═O)Z is selected from the group consisting of:

(i) Formula D, wherein R$_{12}$ is hydrogen and R$_{14}$ is methyl, trifluoromethyl, trifluoromethoxy, 3-, 4- or 5-fluoro, 3-, 4- or 5-chloro, or 3-, 4- or 5-cyano, or 6-hydroxy;

(ii) Formula E, wherein R$_{12}$ is hydrogen and R$_{14}$ is methyl, —CF$_3$, 4- or 5-fluoro, 4- or 5-chloro, or, 4- or 5-cyano, or 2-, 6-hydroxy;

(iv) Formula (C) or any of (K)-(P), wherein R$_{12}$ is hydrogen and R$_{13}$ or R$_{14}$ is F, Cl, trifluoromethyl, trifluoromethoxy, cyano, methylsulfonyl.

15. A compound as claimed in claim 13 wherein radical —C(═O)Z is of Formula C, wherein R$_{12}$ is hydroxyl, —CN or —COOH, and R$_{13}$ is —F, methyl, —CF$_3$, —CN, or methoxy.

16. A compound as claimed in claim 3 wherein R$_4$ and R$_5$ are independently selected from hydrogen, —F, —CN and —Cl.

17. A compound as claimed in claim 3 having formula (IA) or a salt, hydrate, solvate, single enantiomer or N-oxide thereof:

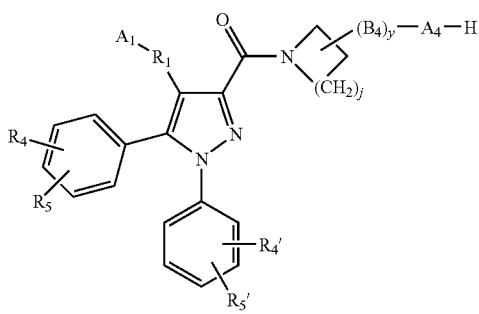

(IA)

wherein $A_1$ is tetrazolyl;

—$R_1$— is —$CH_2$—, —CH(OH)—, —$CHCH_3$—, —$CH_2O$—* wherein the bond indicated by an asterisk is attached to $A_1$ $R_4$, $R_5$, $R_4'$ and $R_5'$ are independently selected from hydrogen, —F, —CN and —Cl;

j is 1, 2 or 3 y is either 0 or 1

$B_4$ is —C($R_{13}$)($R_{14}$)—, —CO—, —$SO_2$—, —O—, or in either orientation —O—C($R_{13}$)($R_{14}$)—, or —$CH_2$—C($R_{13}$)($R_{14}$)—;

$A_4$ is (i) a monocyclic carbocyclic ring, having 3 to 8 ring atoms, optionally substituted with one or more of —F, —Cl, —Br, —CN, —$CF_3$, $C_1$-$C_4$ alkyl, cycloalkyl, —$OR_9$, oxo or —$NR_7R_8$ or $SO_2R_6$, or (ii) a monocyclic heterocyclic ring, having 4 to 8 ring atoms, optionally substituted with one or more of —F, —Cl, —Br, —CN, —$CF_3$, $C_1$-$C_4$ alkyl, cycloalkyl, —$OR_9$, oxo or —$NR_7R_8$ or $SO_2R_6$.

18. A pharmaceutical composition comprising a compound as claimed in claim 3, together with one or more pharmaceutically acceptable carriers or excipients.

* * * * *